United States Patent
Backus et al.

(10) Patent No.: US 9,839,512 B2
(45) Date of Patent: Dec. 12, 2017

(54) PROSTHETIC HEART VALVE HAVING NOTCHED LEAFLET

(71) Applicant: BOSTON SCIENTIFIC SCIMED, INC., Maple Grove, MN (US)

(72) Inventors: Andrew J. H. Backus, Santa Cruz, CA (US); John Lin, Milpitas, CA (US); Shannon Elizabeth Kozinn, Los Gatos, CA (US); Balvir K. Johal, San Jose, CA (US)

(73) Assignee: Boston Scientific, Inc., Maple Grove, MN (US)

( * ) Notice: Subject to any disclaimer, the term of this patent is extended or adjusted under 35 U.S.C. 154(b) by 0 days.

(21) Appl. No.: 15/007,925

(22) Filed: Jan. 27, 2016

(65) Prior Publication Data

US 2016/0220359 A1    Aug. 4, 2016

Related U.S. Application Data

(60) Provisional application No. 62/111,396, filed on Feb. 3, 2015.

(51) Int. Cl.
*A61F 2/24* (2006.01)

(52) U.S. Cl.
CPC .......... *A61F 2/2409* (2013.01); *A61F 2/2412* (2013.01); *A61F 2/2415* (2013.01); *A61F 2220/0075* (2013.01); *A61F 2230/0071* (2013.01); *A61F 2250/0069* (2013.01)

(58) Field of Classification Search
CPC ......... A61F 2/24; A61F 2/2418; A61F 2/2409

USPC .................................................. 623/2.1–2.19
See application file for complete search history.

(56) References Cited

U.S. PATENT DOCUMENTS

| | | | | |
|---|---|---|---|---|
| 5,344,442 A * | 9/1994 | Deac | ..................... | A61F 2/2412 623/2.12 |
| 2002/0116053 A1 * | 8/2002 | Simpson | ............... | A61F 2/2412 623/1.26 |
| 2004/0024452 A1 * | 2/2004 | Kruse | ................... | A61F 2/2415 623/2.13 |
| 2012/0185038 A1 * | 7/2012 | Fish | ....................... | A61F 2/2415 623/2.13 |
| 2014/0277418 A1 * | 9/2014 | Miller | .................. | A61F 2/2403 623/2.17 |
| 2014/0288642 A1 * | 9/2014 | Yoshida | ................. | A61L 27/16 623/2.17 |
| 2015/0216660 A1 * | 8/2015 | Pintor | .................. | A61F 2/2409 623/2.11 |
| 2015/0265401 A1 * | 9/2015 | Braido | ................. | A61F 2/2409 623/2.17 |
| 2016/0199183 A1 * | 7/2016 | Braido | ................. | A61F 2/2412 623/2.18 |
| 2016/0338827 A1 * | 11/2016 | Iobbi | ..................... | A61F 2/2418 |

* cited by examiner

*Primary Examiner* — Suzette J Gherbi
(74) *Attorney, Agent, or Firm* — Seager, Tufte & Wickhem LLP

(57) ABSTRACT

A prosthetic heart valve provided herein can include at least one leaflet having a body portion and two opposite sleeve portions. The body portion can be defined by at least two side edges adjacent each sleeve portion. The at least one leaflet can define at least one notch between at least one of the two side edges and the adjacent sleeve portion, or at least one aperture positioned adjacent at least one side edge and an adjacent sleeve portion.

16 Claims, 18 Drawing Sheets

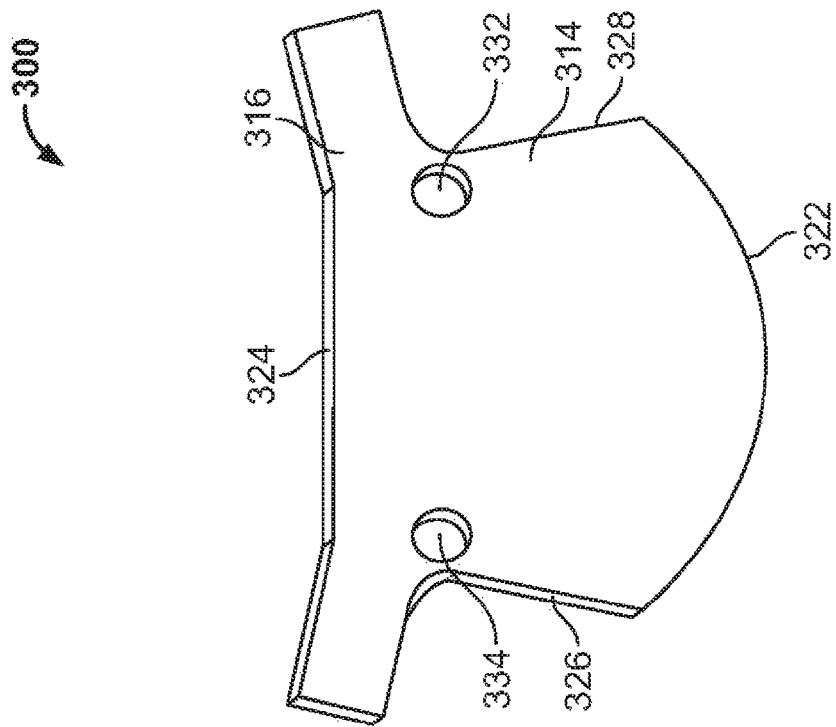
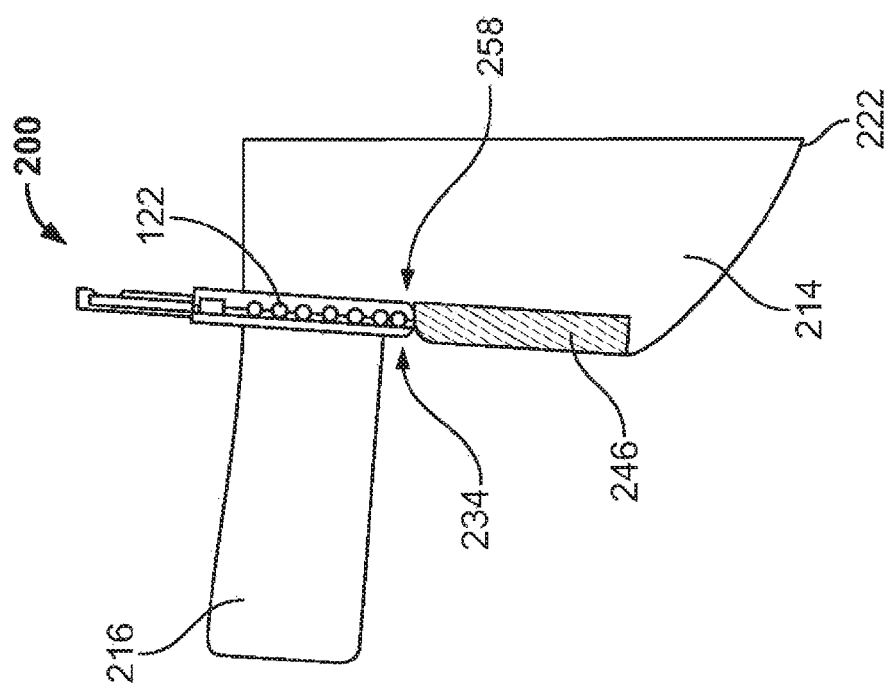

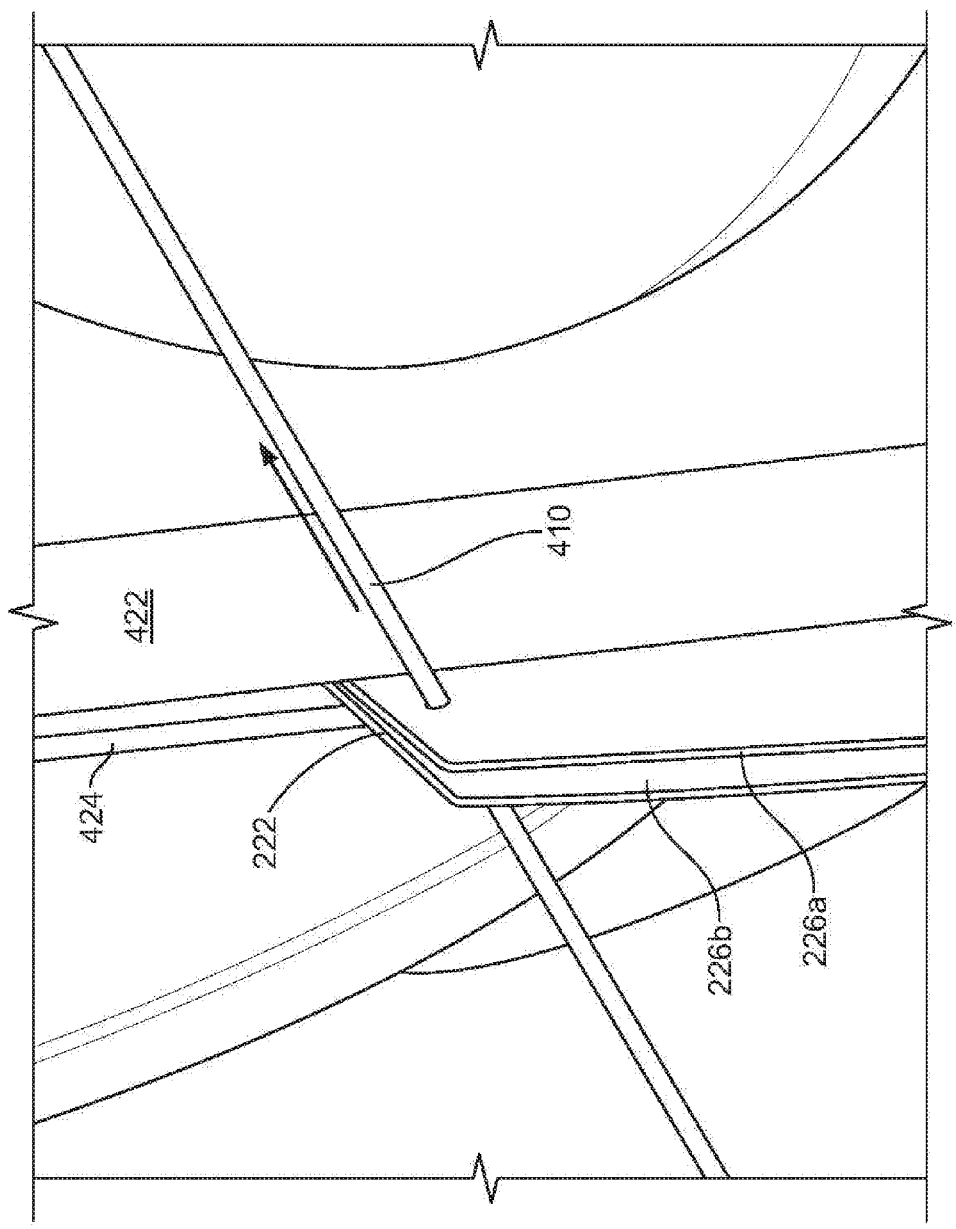

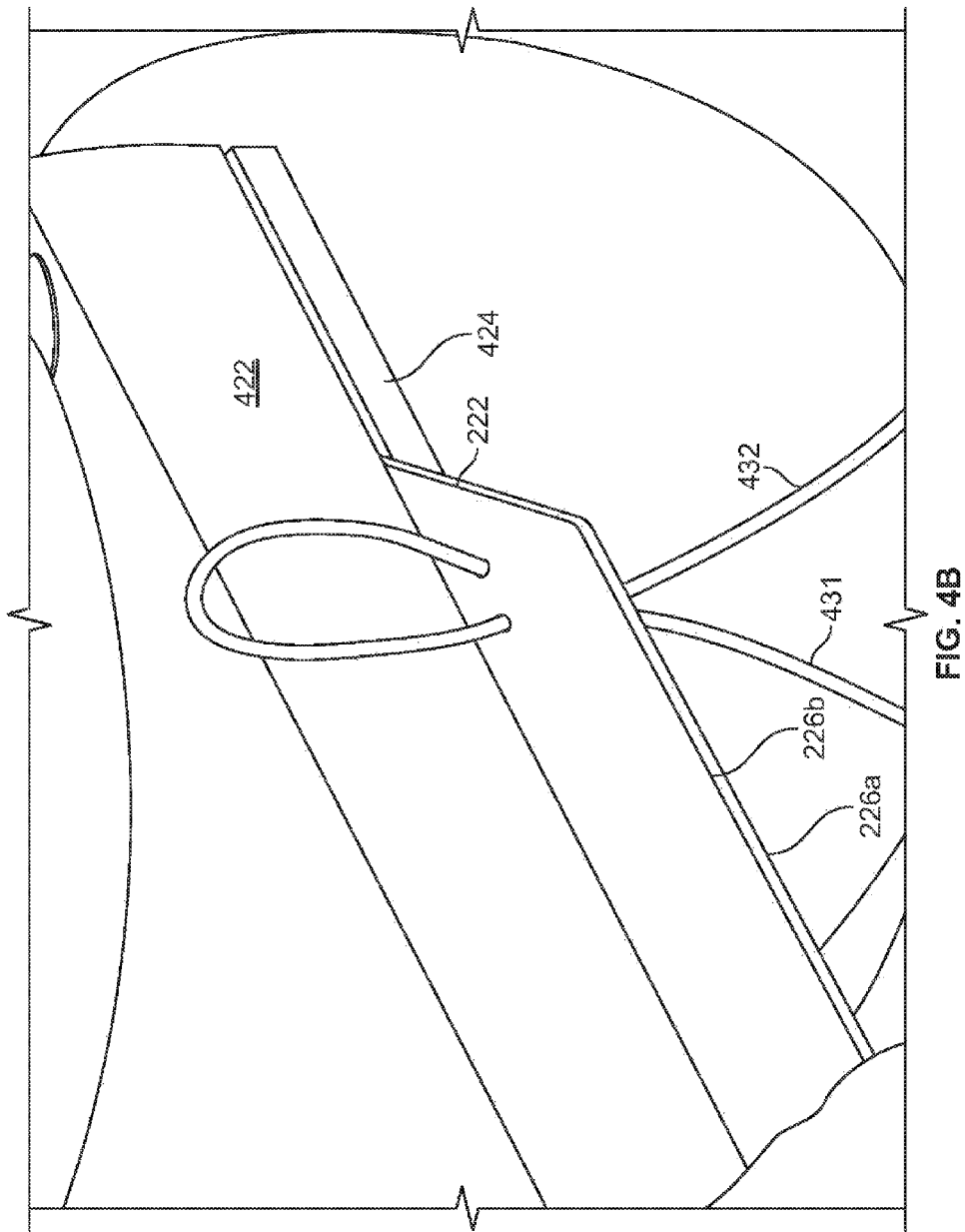

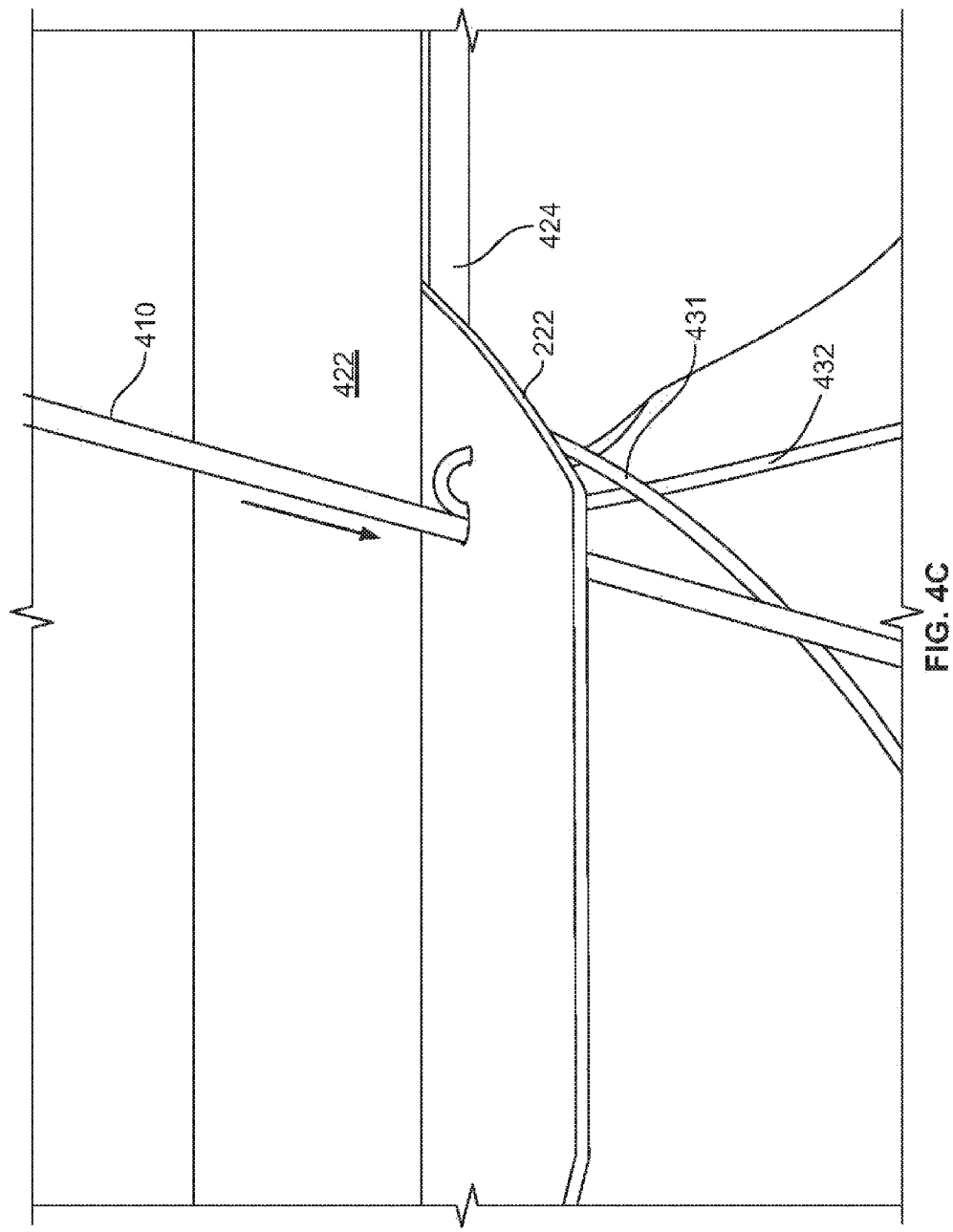

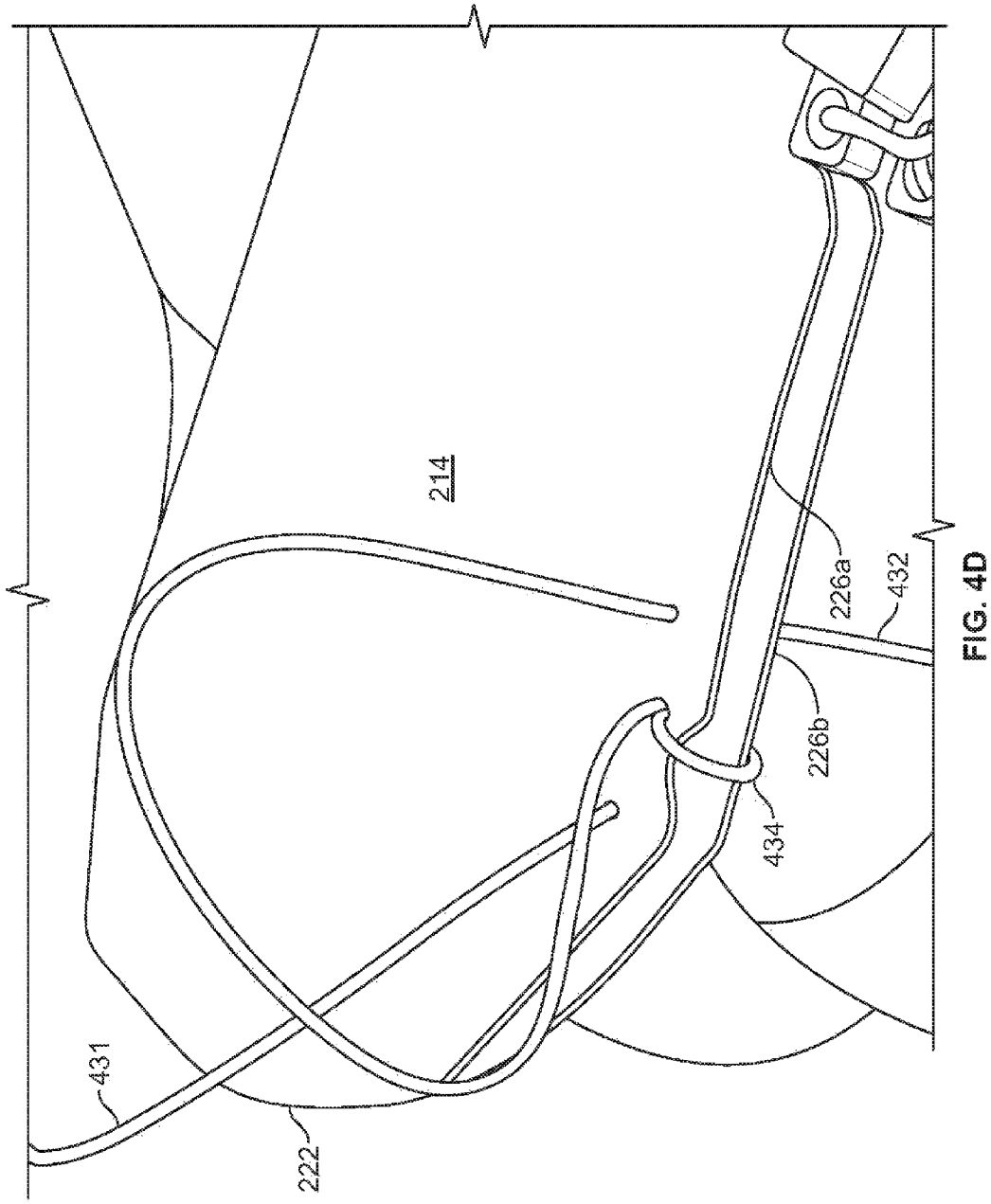

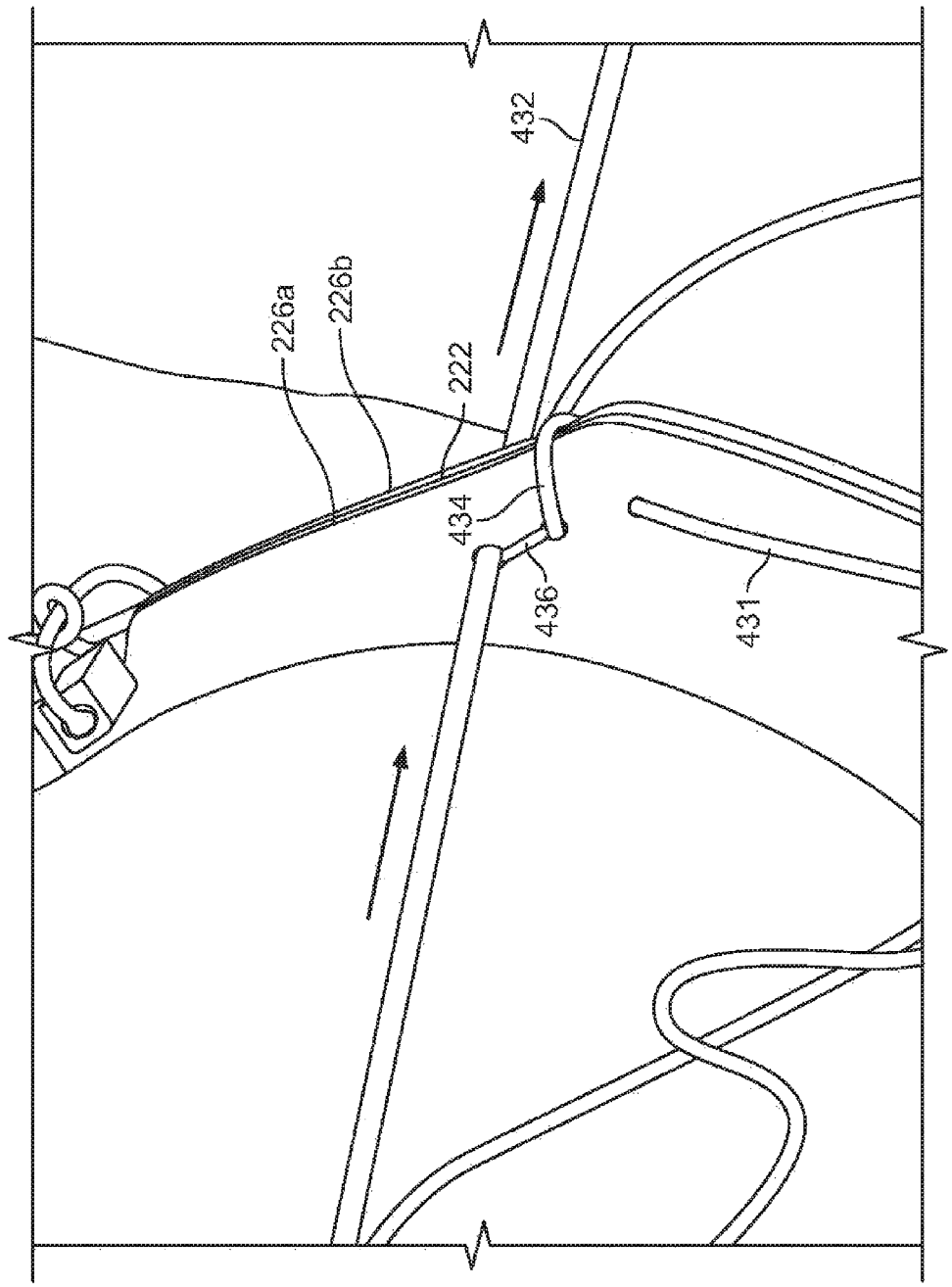

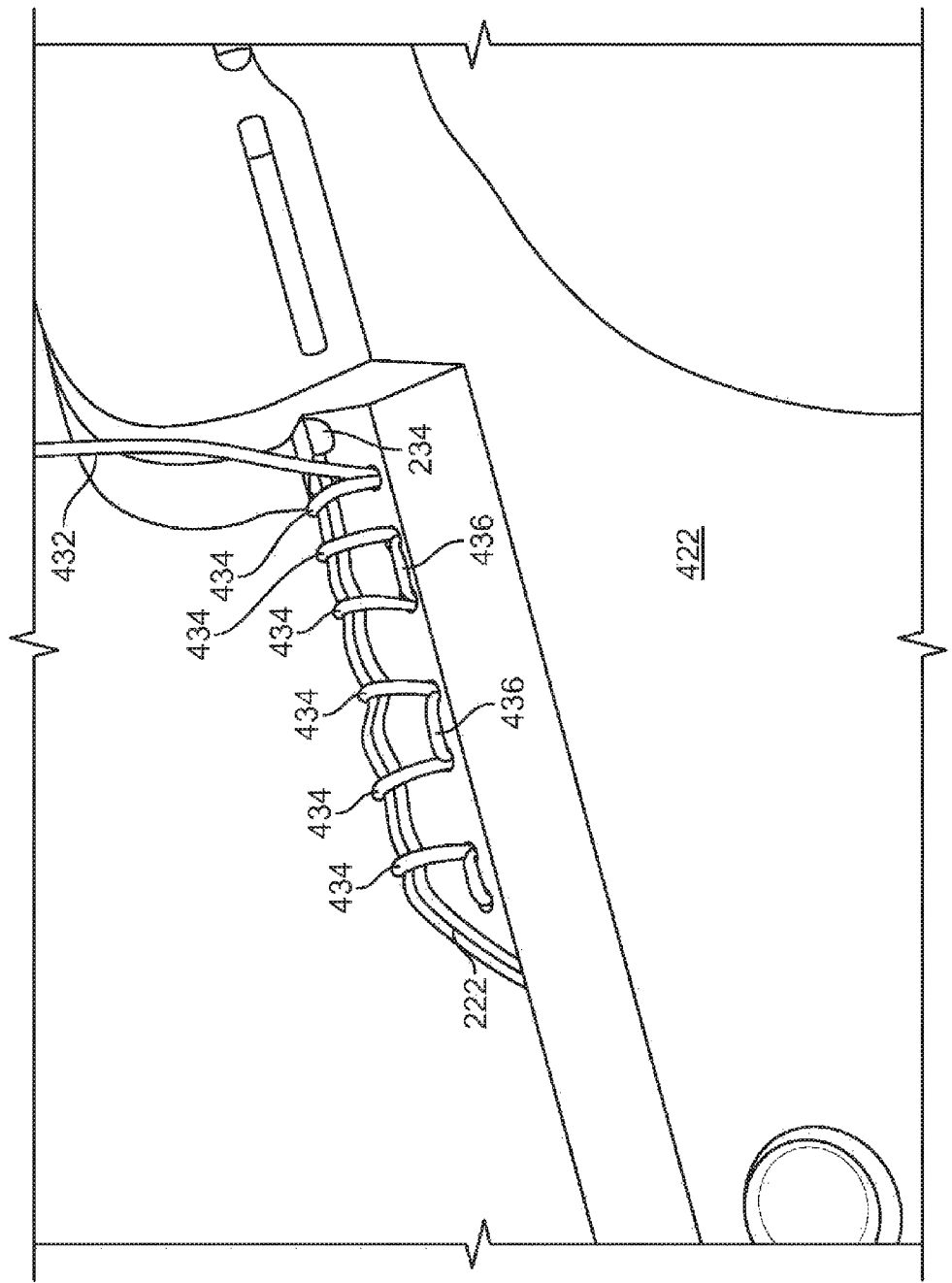

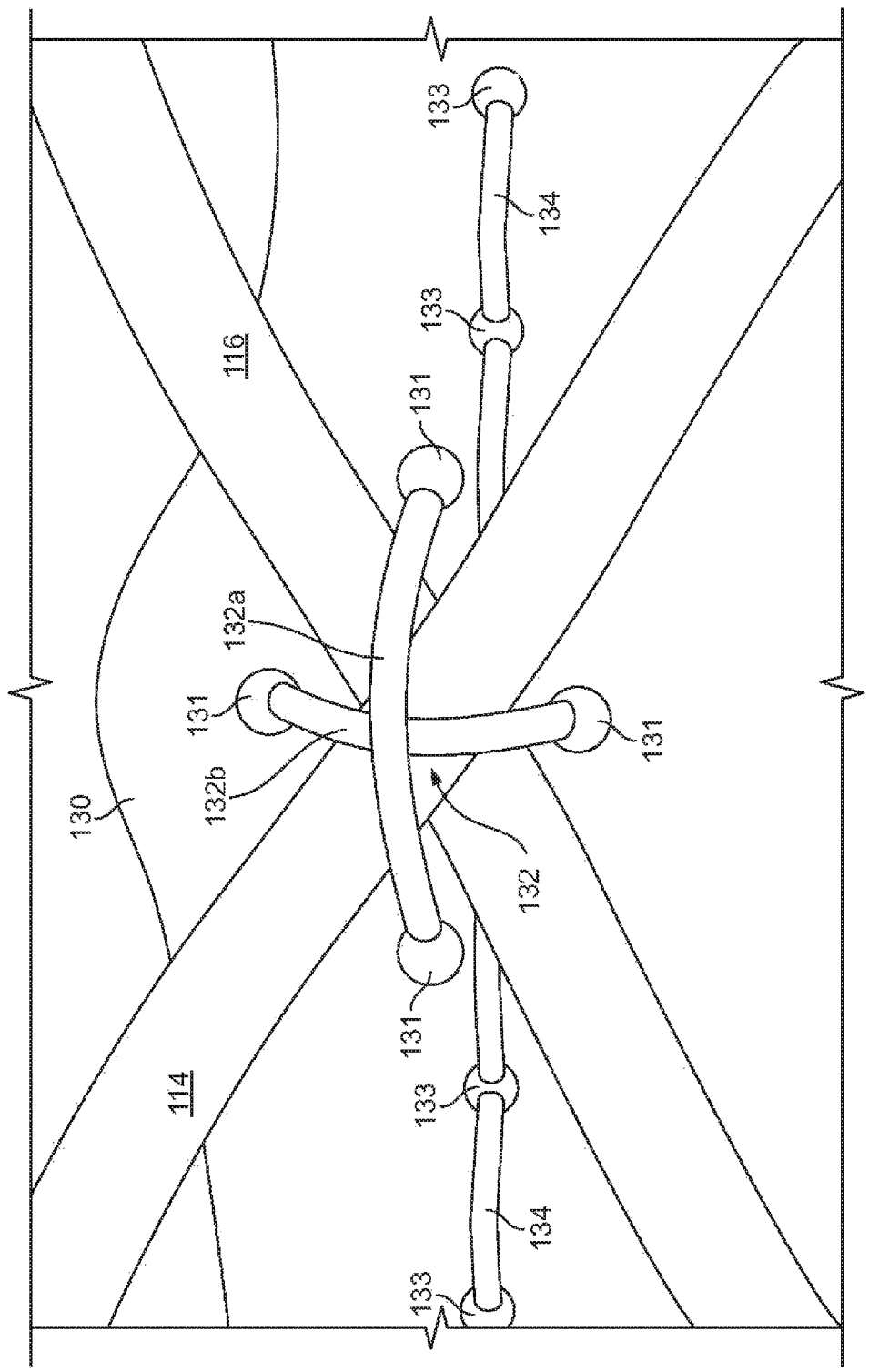

PROSTHETIC HEART VALVE HAVING NOTCHED LEAFLET

RELATED APPLICATIONS

This application claims the benefit of U.S. Provisional Application No. 62/111,396, filed Feb. 3, 2015.

FIELD

This document provides prosthetic heart valves having one or more notched leaflets.

BACKGROUND

The human heart contains four valves: a tricuspid valve, a pulmonic valve, a mitral valve and an aortic valve. The main purpose of the valves is to maintain unimpeded forward flow through the heart and into the major blood vessels connected to the heart, for example, the pulmonary artery and the aorta. As a result of a number of disease processes, both acquired and congenital, any one of the four heart valves may malfunction and result in either stenosis (impeded forward flow) and/or backward flow (regurgitation). Either process burdens the heart and may lead to serious problems, for example, heart failure. Various procedures for fixing or replacing defective heart valves are known in the art. In some cases, artificial heart valves can be implanted in the heart of a patient to replace a diseased or damaged heart valve with a prosthetic equivalent.

Prosthetic heart valves can have a variety of designs. Two major types of prosthetic heart valves include mechanical heart valves and bioprosthetic heart valves. Mechanical heart valves can be made of synthetic materials, such as plastics or metals, while bioprosthetic heart valves can be made of biologic tissue mounted on a fabric covered plastic or metal frame. Bioprosthetic heart valves can include animal tissue, such as porcine or bovine tissue, that has been chemically treated to make the valve suitable for implantation in a human. Bioprosthetic valves do not generally require a patient to undergo anticoagulant therapy, which is typically required when using mechanical valves. As such, there is a need to further improve the design of bioprosthetic valves to retain its functionality during the life of the patient and minimize stenosis and regurgitation.

SUMMARY

Prosthetic heart valves provided herein can have a structure adapted to retain functionality during the life of the patient and minimize stenosis and/or regurgitation by having an improved connection between the different parts of a prosthetic heart valve.

In Example 1, a prosthetic heart valve includes at least one leaflet having a body portion and two opposite sleeve portions. The body portion can be defined by at least two side edges adjacent each sleeve portion. The at least one leaflet can define at least one notch between at least one of the two side edges and the adjacent sleeve portion, or at least one aperture positioned adjacent at least one side edge and an adjacent sleeve portion.

In Example 2, the prosthetic heart valve of Example 1, wherein the prosthetic heart valve comprises three leaflets each defining at least one notch between at least one side edge and an adjacent sleeve portion.

In Example 3, the prosthetic heart valve of one of the preceding examples, wherein the at least one leaflet defines a notch between each of the two side edges and each adjacent sleeve portion.

In Example 4, the prosthetic heart valve of one of the preceding examples, wherein the at least one leaflet is secured to at least a second leaflet along at least one side edge.

In Example 5, the prosthetic heart valve of Example 4, wherein the at least one leaflet is secured to the at least second leaflet by a running stitch.

In Example 6, the prosthetic heart valve of Example 5, wherein the running stitch is a square stitch.

In Example 7, the prosthetic heart valve of one of the preceding Examples, further comprising an expandable member and at least two anchor elements securing each of the sleeve portions to the expandable member.

In Example 8, the prosthetic heart valve of Example 7, wherein the prosthetic heart valve comprises three leaflets and three anchor elements, each leaflet being secured to each of the other leaflets along the side edges of each leaflet.

In Example 9, the prosthetic heart valve of Example 8, further comprising a plurality of support elements each supporting sleeve portions each leaflet along a line approximately aligned with secured portions of the side edges of each leaflet.

In Example 10, the prosthetic heart valve of Example 9, wherein each leaflet is defined by at least two notches, wherein each notch is aligned with the secured portions of the side edges of each leaflet and a supported portion of the sleeve portions.

In Example 11, a prosthetic heart valve comprising at least one leaflet having a body portion and two opposite sleeve portions, the body portion being defined by at least two side edges adjacent each sleeve portion, the leaflet defining two apertures, each aperture being positioned adjacent the side edges and an adjacent sleeve portion, each aperture being adapted to secure one leaflet to an adjacent leaflet.

In Example 12, the prosthetic heart valve of Example 11, wherein the prosthetic heart valve comprises three leaflets each defining at least one apertures, each aperture being positioned adjacent the side edges and adjacent sleeve portions.

In Example 13, the prosthetic heart valve of either Example 11 or Example 12, wherein the at least one leaflet defines an aperture adjacent each of the two side edges and each adjacent sleeve portion.

In Example 14, the prosthetic heart valve of one of Examples 11-13, wherein the apertures are generally circular in shape.

In Example 15, the prosthetic heart valve of one of the preceding Examples, wherein the at least one leaflet comprises bovine or porcine pericardium tissue or a synthetic material.

In Example 16, a prosthetic heart valve comprising at least one leaflet having a body portion and two opposite sleeve portions, the body portion being defined by at least two side edges adjacent each sleeve portion, the at least one leaflet defining at least one notch between at least one of the two side edges and the adjacent sleeve portion.

In Example 17, the prosthetic heart valve of Example 16, wherein the prosthetic heart valve comprises three leaflets each defining at least one notch between at least one side edge and an adjacent sleeve portion.

In Example 18, the prosthetic heart valve of Example 16, wherein the at least one leaflet defines a notch between each of the two side edges and each adjacent sleeve portion.

In Example 19, the prosthetic heart valve of Example 16, wherein the at least one leaflet is secured to at least a second leaflet along at least one side edge.

In Example 20, the prosthetic heart valve of Example 19, wherein the at least one leaflet is secured to the at least second leaflet by a running stitch.

In Example 21, the prosthetic heart valve of Example 20, wherein the running stitch is a square stitch.

In Example 22, the prosthetic heart valve of Example 16, further comprising an expandable member and at least two anchor elements securing each of the sleeve portions to the expandable member.

In Example 23, the prosthetic heart valve of Example 22, wherein the prosthetic heart valve comprises 3 leaflets and three anchor elements, each leaflet being secured to each of the other leaflets along the side edges of each leaflet.

In Example 24, the prosthetic heart valve of Example 23, further comprising a plurality of support elements each supporting sleeve portions each leaflet along a line approximately aligned with secured portions of the side edges of each leaflet.

In Example 25, the prosthetic heart valve of Example 24, wherein each leaflet is defined by at least two notches, wherein each notch is aligned with the secured portions of the side edges of each leaflet and a supported portion of the sleeve portions.

In Example 26, a prosthetic heart valve comprising at least one leaflet having a body portion and at least two opposite sleeve portions, the body portion being defined by at least two side edges adjacent each sleeve portion, the leaflet defining two apertures, each aperture being positioned adjacent the side edges and an adjacent sleeve portion, each aperture being adapted to secure one leaflet to an adjacent leaflet.

In Example 27, the prosthetic heart valve of Example 26, wherein the prosthetic heart valve comprises three leaflets each defining at least one apertures, each aperture being positioned adjacent the side edges and adjacent sleeve portions.

In Example 28, the prosthetic heart valve of Example 26, wherein the at least one leaflet defines an aperture adjacent each of the two side edges and each adjacent sleeve portion.

In Example 29, the prosthetic heart valve of Example 26, wherein the apertures can be generally circular in shape.

In Example 30, the prosthetic heart valve of Example 29, wherein each of the apertures has a diameter between 0.5 mm and 4.0 mm.

In Example 31, the prosthetic heart valve of Example 26, wherein the at least one leaflet comprises bovine or porcine pericardium tissue.

In Example 32, the prosthetic heart valve of Example 26, wherein the at least one leaflet comprises a synthetic material.

In Example 33, the prosthetic heart valve of Example 26, wherein each of the apertures is shaped and sized to accommodate attachment of at least one post leg compression element.

In Example 34, the prosthetic heart valve of Example 26, further comprising at least three anchoring elements securing sleeve portions of each leaflet to the expandable member, each sleeve portion being supported along a portion aligned with secured side edge portions of each leaflet.

In Example 35, a prosthetic heart valve includes an expandable tubular member three leaflets, at least three anchoring elements and a tubular seal. Each leaflet can have a body portion and two opposite sleeve portions, the body portion of each leaflet being defined by two side edges adjacent each sleeve portion. Each leaflet can also define two notches, each notch being positioned between a side wall and an adjacent sleeve portion. Each leaflet can be secured to the other two leaflets along the side edges and each notch can be aligned with secured sidewall portions of each leaflet. The at least three anchoring elements can secure sleeve portions of each leaflet to the expandable member, each sleeve portion being supported along a portion aligned with secured sidewall portions of each leaflet. The tubular seal can be secured to a bottom edge of each leaflet and along an outer portion of the expandable tubular member.

Prosthetic heart valves provided herein can additionally have a reduced unexpanded profile. In some cases, prosthetic heart valves provided herein include a plurality of anchor elements. In some cases, anchor elements can be secured to an expandable tubular member. In some cases, the expandable tubular member can be a braided stent. In some cases, prosthetic heart valves provided herein include three or more leaflets. In some cases, the leaflets can have a body portion and sleeve portions one or both sides. In some cases, sides of the body portions can be secured together and sleeve portions secured to anchor elements (e.g., anchor elements attached to a braided stent). In some cases, anchor elements can include post leg support structures adapted to compress and support sleeve portions of leaflets. In some cases, prosthetic heart valves provided herein can include a tubular seal. In some cases, the tubular seal can be secured to bottom edges of body portions of the leaflets. In some cases, the seal can be secured to a blood inlet side of an expandable member.

In some aspects, prosthetic heart valves provided herein include leaflets having one or two notches in the body portion adjacent to one or both of the sleeve portions.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a perspective view of the heart valve connected to the deployment device. FIG. 1B is a side view of the exemplary prosthetic heart valve. FIGS. 1C-1H illustrate how the exemplary heart valve provided herein can be delivered by the deployment device.

FIGS. 2A-2C illustrates an exemplary leaflet, which can be used in prosthetic heart valves provided herein. FIG. 2A illustrates a rounded notch in a leaflet where a leaflet can be secured to an adjacent leaflet. FIGS. 2B and 2C illustrate a portion of an exemplary leaflet for prosthetic heart valves. FIG. 2B depicts the rounded notch in an armpit of a leaflet. FIG. 2C depicts attachment elements in the armpit of the leaflet.

FIG. 3 illustrates another exemplary leaflet, which can be used in prosthetic heart valves provided herein. FIG. 3 depicts apertures in a body of the exemplary leaflet.

FIGS. 4A-4G illustrate how adjacent leaflets can be stitched together in prosthetic heart valves provided herein.

FIGS. 5A-5C illustrate a cross stitch provided herein for connecting a seal to a braided stent in an exemplary prosthetic heart valve provided herein. FIG. 5A shows a front view of a seal having apertures and stitch patterns used for securing the seal to the braided stent. FIG. 5B depicts a close up view of a cross stitch and a portion of a circumferential stitch used for securing the seal to the braided stent. FIG. 5C depicts a cross-sectional view showing the cross stitch and a portion of the circumferential stitch.

Like reference symbols in the various drawings indicate like elements.

DETAILED DESCRIPTION

Prosthetic heart valves provided herein can include leaflets arranged to limit excessive loading and abrasion on the leaflets material (e.g., leaflet biologic tissue). Prosthetic heart valves provided herein can include leaflets formed of biologic tissue or synthetic material cut into individual leaflets, which are then secured together to simulate the function of a natural heart valve. Prosthetic heart valves provided herein can include leaflets cut to include a body portion and two sleeve portions.

Prosthetic heart valves provided herein can have two distinct regions of attachment between the leaflets: a leaflet-leaflet stitch between side edges of body portions of the leaflets and post leg support structures compressing sleeve portions of the leaflets together. Post leg support structures can provide support and structure to the free edge of the valve as well as provide foreshortening force to maintain the valve in its locked configuration. The leaflet-leaflet stitch is intended to stop leakage through the leaflets during valve closure and maintain a low profile during valve crimping. In order for the foreshortening force to be applied to both inflow and outflow sides of the valve, post leg support structures can be secured together at bottom portions (e.g., via a suture) below the sleeve portions of the leaflets.

Prosthetic heart valves provided herein can include post leg support structures that support sleeve portions of leaflets along a line aligned with a line of leaflet-leaflet stitches. Providing post leg support structures that support the leaflets along the same line established by the leaflet-leaflet stitches can reduce loading on the leaflet tissue by avoiding the creation of stress concentrators. Passing a suture through the leaflets to connect the post leg support structures, however, can result in abrasion to the leaflet that can initiate tears in the leaflet material. Prosthetic heart valves provided herein define notches and/or apertures in the leaflets to allow a bottom connection of post leg support structures such that the post leg support structures support sleeve portions of the leaflets along the same line established by the leaflet-leaflet stitches. Accordingly, prosthetic heart valves provided herein can exhibit less leaflet failure due to improved loading on the leaflets while avoiding abrasion of the leaflets.

Figure 1A:
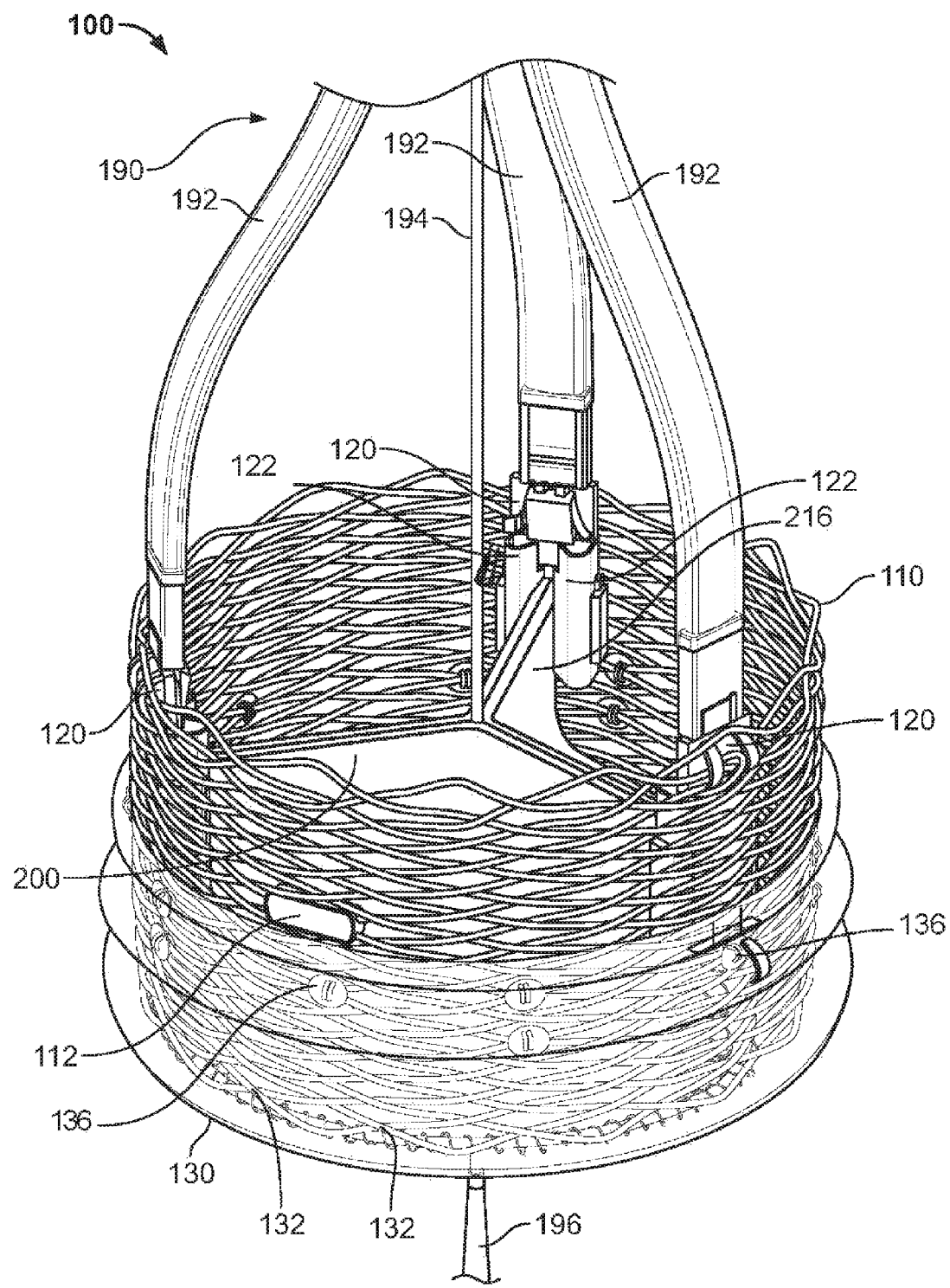
FIGS. 1A-1H illustrate an exemplary prosthetic heart valve and an exemplary deployment device provided herein.
Figure 1B:
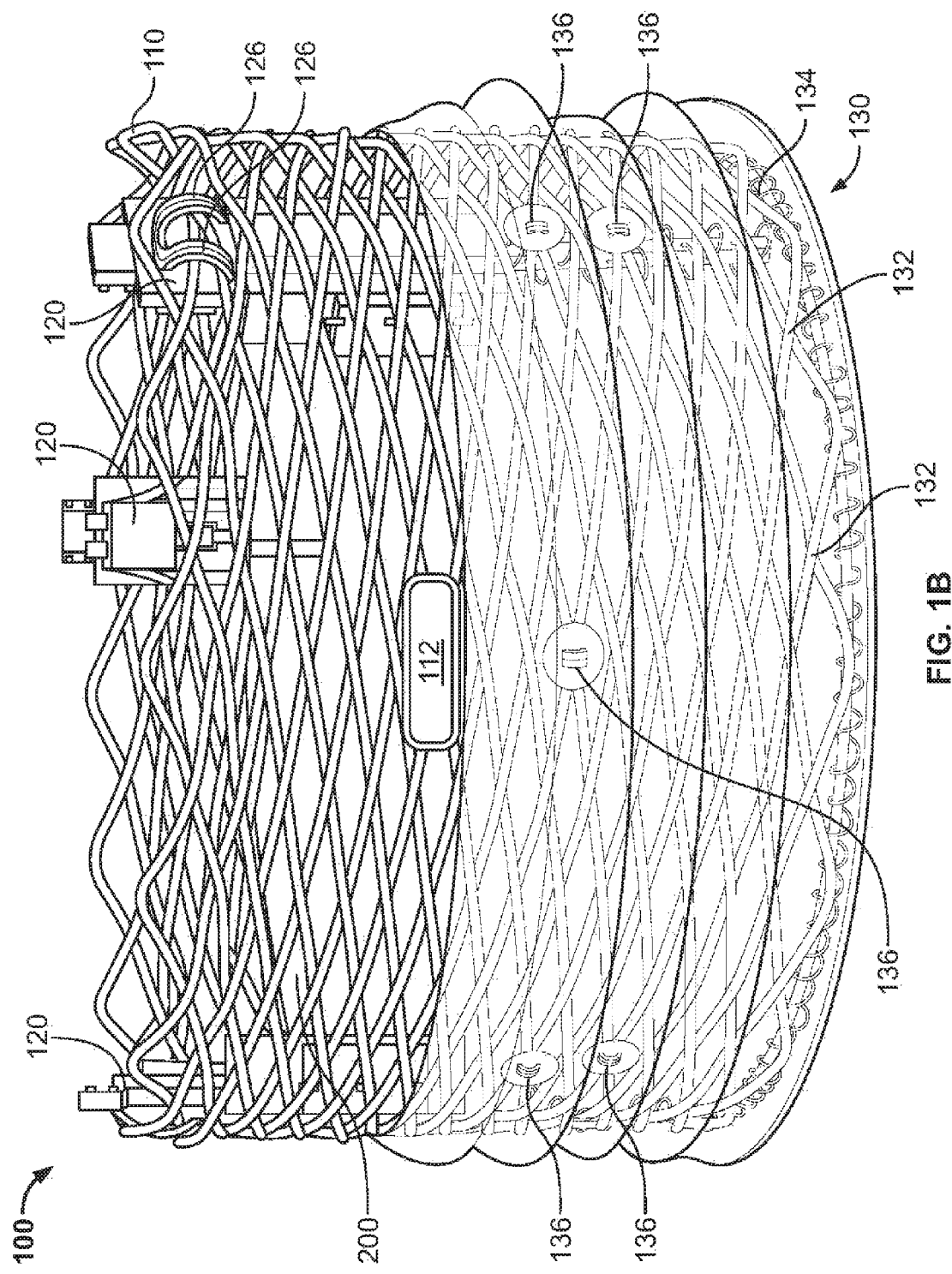
Figure 1C:
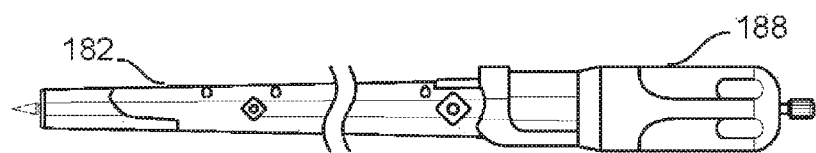
Figure 1D:
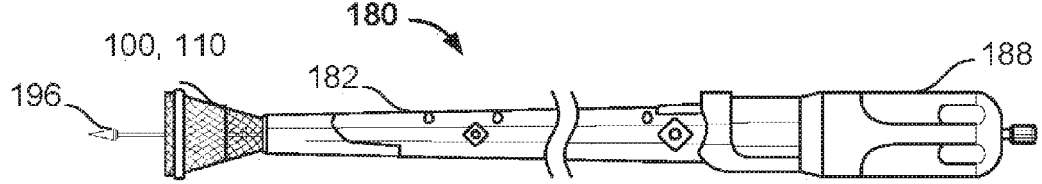
Figure 1E:
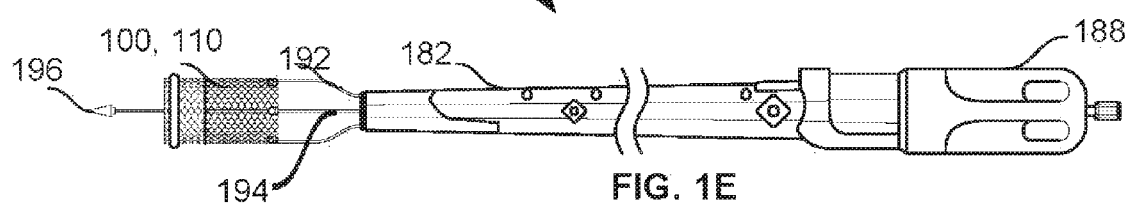
Figure 1F:
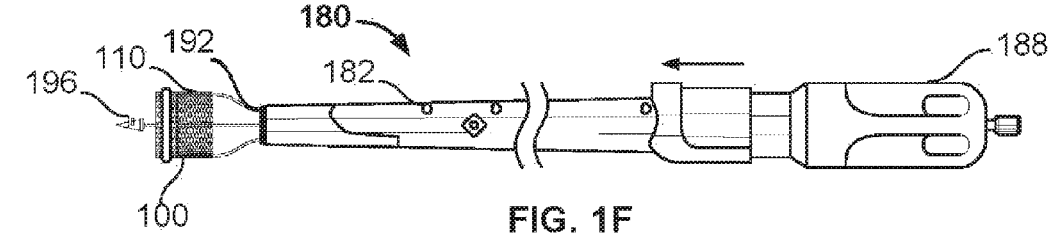
Figure 1G:
Figure 1H:
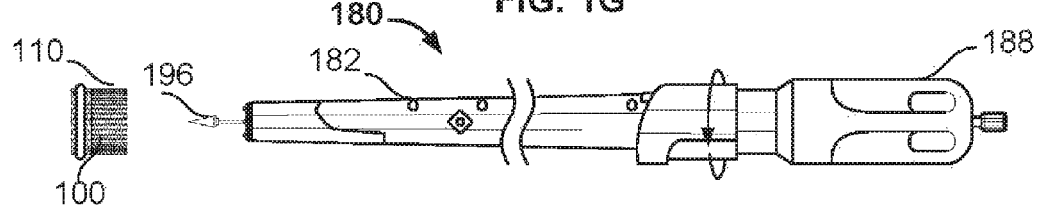

FIGS. 1A and 1B illustrate an exemplary prosthetic heart valve 100 provided herein. FIGS. 1C-1H depict how prosthetic heart valve 100 is deployed. FIG. 1A is a perspective view of prosthetic heart valve 100 connected to a deployment device 190. FIG. 1B is a side view of prosthetic heart valve 100. As shown, prosthetic heart valve 100 includes an expandable member 110, three leaflets 200, three anchor elements 120 that secure sleeve portions 216 of leaflets 200 to expandable member 110, and a tubular seal 130 secured around a blood inflow end of prosthetic heart valve 100. Anchor elements 120 can include post leg compression elements 122 and clamping support structures 126 adapted to provide support along opposite sides of the sleeve portions 216. Expandable member 110 in FIGS. 1A-1D is a braided stent, which is adapted to transition between a restricted state having a smaller diameter and an expanded state having a larger diameter. Expandable member 110 can be self-expanding, mechanically expanded, or a combination thereof.

FIGS. 1C-1H depict how an exemplary heart valve delivery system can deliver the prosthetic heart valve provided herein. As shown in FIGS. 1C-1H, prosthetic heart valve 100 can be deployed using a heart valve delivery system 180. System 180 can include a sheath 182 for retaining the prosthetic heart valve 100 with the expandable member 110 in a restricted state. Within sheath 182, anchor elements 120 (FIGS. 1A and 1B) can be connected to pushing prongs 192 and a pull line 194 can be connected to a nose cap 196, or end cap, which is positioned at the end of the sheath 182. As shown in FIG. 1A, the pull line 194 can extend through expandable member 110 and through the valve opening between the leaflets 200. As shown by FIGS. 1D-1H, once a distal end of sheath 182 is delivered through the circulatory system to an appropriate location (e.g., within the heart), prosthetic heart valve 100 can be deployed. By advancing pushing prongs 192 and pull line 194 relative to sheath 182, prosthetic heart valve 100 can be pushed out of the sheath 182. In some cases, expandable member 110 can self-expand upon exiting sheath 182. In some cases, expandable member 110 can self-expand to a first intermediate diameter, and system 180 can mechanically expand expandable member 110 to a larger deployment diameter. For example, anchor elements 120 can include a locking mechanism to clip a portion of expandable member when the expandable member 110 is expanded to a predetermined locking diameter. In some cases, system 180 can mechanically expand expandable member 110 to a predetermined locking diameter. In some cases, system 180 can compress expandable member 110 between pushing prongs 192 and nose cap 196 by moving pull line 194 relative to pushing prongs 192. The predetermined locking diameter can be adapted to set the diameter of the prosthetic heart valve 100 during implantation. After prosthetic heart valve 100 is set, system 180 can move pull line 194 and nose cap 196 relative to pushing prongs 192 to move the end cap through the opening between leaflets 200 in prosthetic heart valve 100. Pushing prongs 192 can then be retracted from anchor elements 120 and retracted into sheath 182. In some cases, pushing prongs 192 can include a shape member material adapted to help radially expand expandable member 110 as the expandable member 110 exits sheath 182. A control handle 188 can be used to control the relative movements of sheath 182, pushing prongs 192, and pull wire 194. Prosthetic heart valves provided herein can be adapted to mitigate damage that might otherwise occur to valves during delivery and implantation.

In some cases, one or more radiopaque markers can be secured to prosthetic heart valves provided herein. As shown in FIGS. 1A and 1B, expandable member 110 includes a radiopaque marker 112. Any suitable radiopaque material (such as platinum, palladium, gold, tantalum, or alloys thereof) can be used as the radiopaque material in radiopaque marker 112. One or more radiopaque markers can be used with an imaging system to help a physician ensure that a valve is set in an appropriate location. In some cases, prosthetic heart valves provided herein include at least three radiopaque markers.

As shown in FIG. 1A, prosthetic heart valve 100 can include a plurality of leaflets 200. In some cases, as shown, prosthetic heart valve 100 includes three leaflets 200. In some cases, prosthetic heart valves provided herein can have any suitable number of leaflets, such as two, three, four, five, or more leaflets. In some cases, leaflets 200 are secured to one another. In some cases, leaflets 200 can be secured to one another via a plurality of sutures. Leaflets 200 can be sutured alongside edges of a body portion of each leaflet. In some cases, prosthetic heart valves provide herein can include a single line of sutures, which can be adapted to minimize leaks, minimize the width of a seam, and/or minimize the profile of a replacement heart valve during percutaneous insertion. In some cases, prosthetic heart valves provide herein can include multiple lines of sutures.

Expandable member 110 can have any suitable structure, arrangement, or material. In some cases, expandable member 110 can include a braided wire stent. For example, U.S. Publication Number 2005/0143809, titled, "Methods and Apparatus for Endovascularly Replacing a Heart Valve," and filed on Nov. 5, 2004, which is herein incorporated by reference for its disclosure of possible structures and materials for a braided wire stent, discloses a braided wire stent. In some cases, expandable member 110 includes a shape memory material (e.g., a nickel-titanium alloy or a cobalt-chromium alloy).

Figure 2B:
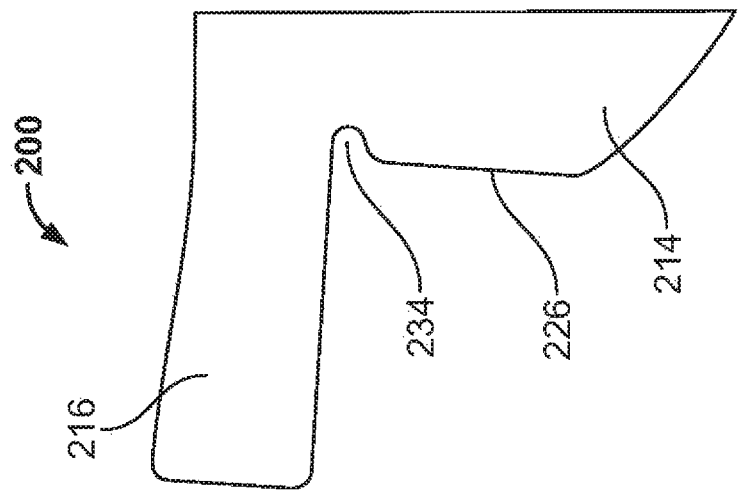
Figure 2A:
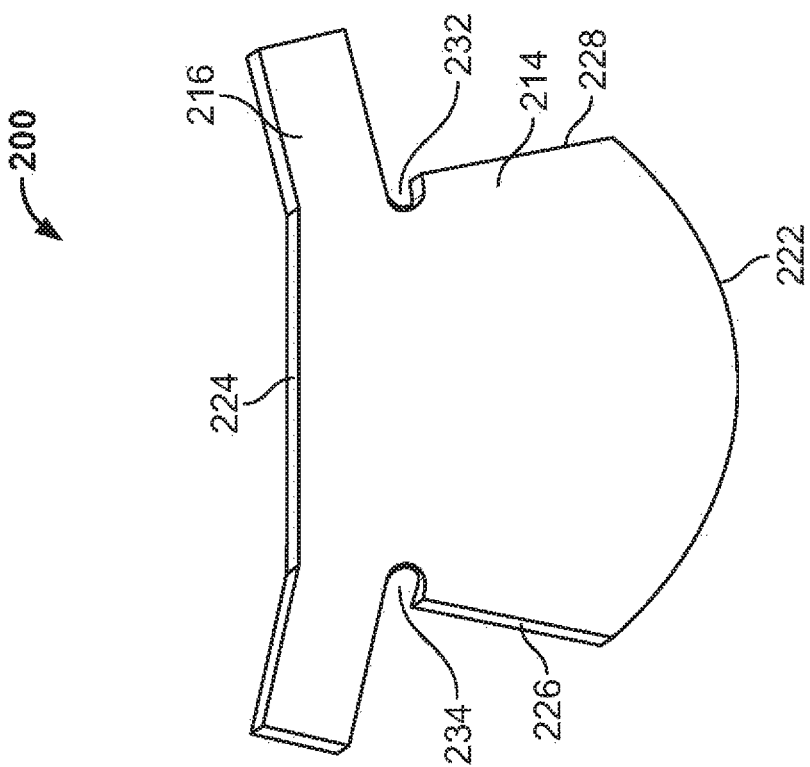

Referring to FIGS. 2A-2C, a leaflet 200 can include a body portion 214 and sleeve portions 216. In some cases, the body portion 214 has a bottom edge 222, a first side edge 226, a second side edge 228, and a free edge 224. Leaflet 200 further includes a front (i.e., the side that blood flows toward), a back (i.e., the side that blood flows away from), a first side adjacent to the first side edge 226, and a second side adjacent to the second side edge 228. In some cases the front of the leaflet 200 has a different texture than the back. In some cases, for example, the back of the leaflet may be prone to calcium build due to its cusp-shaped surface, therefore it can be beneficial to have a textured surface on the back of the leaflet to mitigate valve calcification issues. In some cases, however, having the back with a non-textured surface can mitigate calcification issues. In some cases, the leaflet 200 is made from tissue obtained from an animal, e.g., a pig or a cow. In some cases, leaflet 200 is made from bovine pericardium. Leaflets 200 can also be made from a synthetic material. Leaflets 200 can be assembled into a heart valve by aligning the opposite side regions of at least two adjacent leaflets 200 and stitching the leaflets 200 together along stitch line 246, as shown in FIG. 2C.

As shown in FIGS. 2A-2C, a prosthetic heart valve can include at least one leaflet 200 having a body portion 214 and two opposite sleeve portions 216. The body portion 214 can be defined by two side edges 226, 228 adjacent each sleeve portion 216. The at least one leaflet 200 can define at least one notch 232, 234 between at least one of the two side edges 226, 228 and the adjacent sleeve portion 216. In other words, each notch 232, 234 can be located along the side edges 228, 226 at a location that is adjacent to the sleeve portions 216, at an armpit of the leaflet 200, as depicted in FIGS. 2A and 2B. In some cases, leaflet 200 can define a notch 232, 234 generally along the side edges 228, 226. In some cases, a notch 232, 234 can be defined along the sleeve portion 216. In some cases, multiple notches 232, 234 can be located along the sleeve portion 216 or one of the side edges 228, 226, and/or at the armpit of the leaflet 200.

As shown in FIGS. 2A and 2B, the body portion 214 of the leaflet can have a conical frustum shape defined by a bottom edge 222, the first side edge 226, the second side edge 228, and a free edge 224. In some cases, other suitable shapes for the body portion can be contemplated, for example, a generally square, rectangular, triangular or trapezoidal shaped body portion.

The sleeve portions, as shown in FIGS. 2A-2C, can extend outwardly from the body portion of the leaflet 200. Each sleeve portion may be angled away from free edge of the body portion. Sleeve portions can be generally rectangular-shaped extensions with lateral ends. In some cases, the sleeve portions can have rounded ends.

Still referring to FIGS. 2A-2C, notches 232, 234 can be generally U-shaped. Other suitable notch shapes can include, but are not limited to, a V-shaped, Z-shaped, rectangular-shaped and an oval-shaped notch. Notches can also have rounded edges to smooth the transition between a notch and the side edges 228, 226 of the leaflet 200. Notches 232, 234 can have a length dimension that can range from about 0.02 inches to about 0.20 inches (or from about 0.5 millimeters (mm) to about 4 mm).

Referring to FIG. 2C, notches 232, 234 can be shaped and sized to accommodate attachment of post leg compression elements 122. Post leg compression elements 122 can be a part of anchor elements 120 (shown in FIGS. 1A and 1B) that compress and restrain sleeve portions 216 along the same line as the stitch line 246. A suture 258 can be used to apply an appropriate and consistent compressive force between the post leg compression elements 122 in order to prevent leakage through sleeve portions 216 of the leaflets 200. Sutures that pierce the body portion 214 at or near the armpit of the leaflet, however, can pull, stretch and abrade the surrounding adjacent tissue, creating stress concentrations at or near the armpit of the leaflet. Stress concentrators can result in tears forming in the leaflet material. Using notches 232 and 234 and post leg compression elements 122, however, can minimize potential heart valve tearing caused by sutures at or near the armpit location. Notches 232, 234 can be positioned proximate to the post leg compression elements near the armpit of the leaflet, e.g., between at least one of the two side edges 226, 228 and the adjacent sleeve portion 216, to create enlarged openings that suture 258 can pass therethrough without pulling or stretching the adjacent tissue. Accordingly, a notched leaflet 200 can improve valve opening capabilities and the reliability of prosthetic heart valves provided herein.

FIG. 3 illustrates another exemplary leaflet, which can be used in prosthetic heart valves provided herein. As shown in FIG. 3, leaflet 300 can include a body portion 314 and at least two opposite sleeve portions 316. The body portion 314 can be defined by at least two side edges 326, 328 adjacent each sleeve portion 316. Leaflet 300 can define two apertures 332 and 334. Each aperture 332, 334 can be positioned adjacent the side edges 326, 328 and an adjacent sleeve portion 316. Each aperture 332, 334 can be adapted to secure one leaflet to an adjacent leaflet.

In some cases, the body portion 314 has a bottom edge 322, a first side edge 326, a second side edge 328, and a free edge 324. Leaflet 300 further includes a front, a back, a first side adjacent to the first side edge 326, and a second side adjacent to the second side edge 328. In some cases, the front of the leaflet 300 has a different texture than the back. In some cases, this occurs where the leaflet 300 is made from pig, cow, or other natural animal tissue. In some cases, leaflet 300 is made from bovine pericardium. Leaflets 300 can also be made from a synthetic material. Leaflets 300 can be assembled into a heart valve by aligning the opposite side regions of at least two adjacent leaflets 300 and stitching the leaflets 300 together along stitch line 246, as shown in FIG. 2C.

As shown in FIG. 3, leaflet 300 defines apertures 332 and 334 adjacent the side edges 328, 326 and adjacent the sleeve portions 316. Apertures 332 and 334 can be generally circular in shape. Other suitable aperture shapes can include, for example, a rectangular, an oval, a triangular, or a diamond shape. In some cases, apertures 332, 334 can have a length dimension or a diameter from about 0.02 inches to about 0.20 inches (or from about 0.5 mm to about 4 mm). In some cases, one or more apertures 332, 334 can be located in the side edges 328, 326 and/or the sleeve portions 316 of the leaflet 300. In some cases, multiple apertures can be located in a region that is adjacent to the side edges 328, 326 and the sleeve portions 316.

Apertures 332, 334 in the leaflets 300 can allow one leaflet to be secured to an adjacent leaflet. Similar to the notches discussed above, apertures 332 and 334 can be shaped and sized to accommodate attachment of post leg compression elements 122. Referring back to FIGS. 1A and 1B, post leg compression elements 122 can be a part of anchor elements 120 that compress and restrain sleeve portions 216 along the same line as the stitch line 246. A suture 258 can be used to apply an appropriate and consistent compressive force between the post leg compression elements 122 in order to prevent leakage through sleeve portions 216 of the leaflets 200. As already discussed herein, sutures that pierce the body portion 214 at or near the armpit of the leaflet can create stress concentrations at or near the armpit of the leaflet that may result in tearing. Apertures 332 and 334 and post leg compression elements 122, however, can minimize this potential tearing caused by sutures near the armpit location. Apertures 332, 334 can be positioned proximate to the post leg compression elements near the armpit location to create enlarged openings that suture 258 can pass therethrough without pulling or stretching the adjacent tissue. Accordingly, leaflets 300 used in prosthetic heart valves provided herein can improve the reliability of prosthetic heart valves provided herein.

FIGS. 4A-4G depict how leaflets 200 can be connected (or jointed) with an improved stitch discussed herein. As shown, stitch 446 can be a single continuous line stitch traveling along a stitch line in a forward direction and back in a reverse direction. In some cases stitch 446 can run along a leaflet from a bottom edge to a side edge of the leaflet (e.g., bottom edge 222 to side edge 226 of leaflet 200 in FIG. 2A-2B). In some cases stitch 446 can run from a side edge to a notch of a leaflet (e.g., side edge 226 to notch 234 of leaflet 200 in FIG. 2A-2B).

As shown in FIGS. 4D-4G, stitch 446 can include a plurality of perpendicular loop segments 434 extending through an aperture in the two leaflets, around outer side edges of the two attached leaflets, and back through the aperture. Stitch 446 can include a plurality of parallel segments 436 extending between adjacent apertures along the stitch line. Stitch 446 can include two perpendicular loop segments 434 extending through apertures formed in the stitch line. In some cases, a first perpendicular loop segment 434 for a first aperture in the stitch line is formed when the stitch is formed in the forward direction and a second perpendicular loop segment 434 for the first aperture is formed in the reverse direction. In some cases, parallel segments 436 made in a forward direction alternate between opposite sides of the two leaflets between each aperture in the stitch line. In some cases, parallel segments 436 made in a reverse direction are formed on an opposite side of the two leaflets from parallel segments 436 made in a forward direction. In some cases, opposite parallel segments 436 made in the forward and reverse directions can provide a continuous compressive force along the entire length of the stitch line. Perpendicular loop segments 434 can provide compressive force to reinforce a seal formed between the two leaflets along the stitch line.

Stitch 446 can include any appropriate number of perpendicular loop segments formed through any appropriate number of apertures. As shown, stitch 446 includes six perpendicular loop segments formed through six apertures (two perpendicular loop segments per aperture). In some cases, stitch 446 can include up to twelve perpendicular loop segments formed through six or more apertures. In some cases, a stitch connecting side edge segments of leaflets can be formed using between 3 and 20 apertures and include between 3 and 40 perpendicular loop segments. In some cases apertures can be positioned from about 0.008 inches to about 0.4 inches apart (about 0.2 mm to about 10 mm apart). In some cases, apertures can be positioned from about 0.008 inches to about 0.4 inches (about 0.2 mm to about 10 mm) away from the side edges of the leaflets.

Figure 4G:
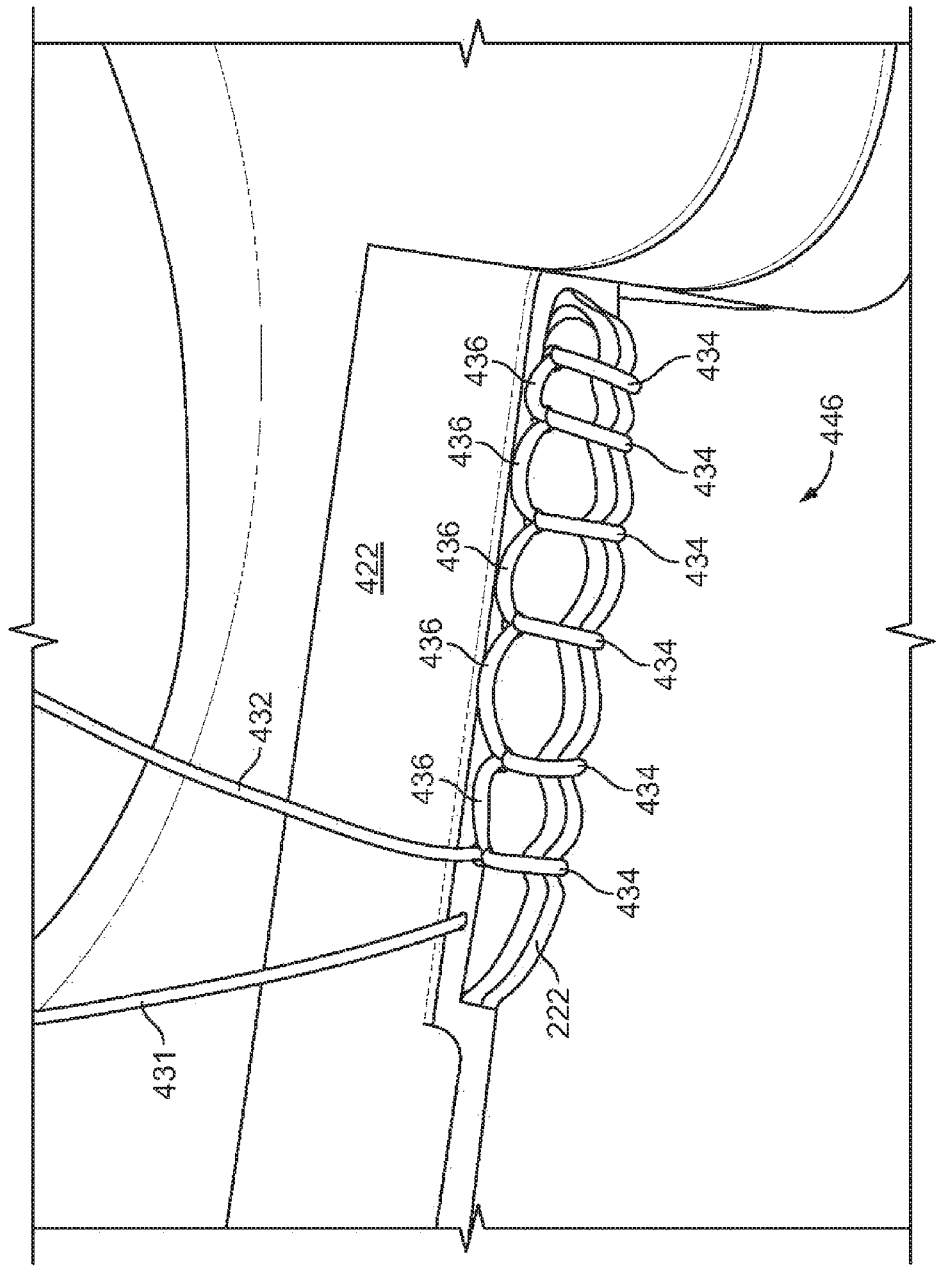

Stitch 446 can be formed in a process depicted in FIGS. 4A-4G. As shown in FIG. 4A, a thread needle 410 can be passed through aligned leaflet side edges 226a and 226b to create a first aperture at a location near bottom edges 222, e.g., a location approximately 1 mm from the bottom edges 222. The leaflet side edges 226a and 226b can be retained in a desired configuration by clamping the leaflets between clamp sides 422 and 424. Needle 410 pulls a leading end 431 of a thread 432 through the first aperture. As shown in FIG. 4B, needle 410 can then form a second aperture adjacent to the first aperture along the stitch line (towards the leaflet sleeve portion) about 0.5 mm away from the first aperture to pull leading end 431 of thread 432 through the second aperture to form a first parallel segment. As shown in FIG. 4C, a perpendicular loop segment 434 can be made by guiding needle 410 around the leaflet side edges and re-enter the second aperture from a backside. Thread 432 can be pulled through the second aperture until it sits firmly against the leaflet material (e.g., leaflet pericardium tissue). FIG. 4D shows a second parallel segment, which can be made by pushing needle 410 through leaflet tissue along the stitch line to form a third aperture approximately 1 mm from the second aperture (towards the sleeve segments of the leaflet). As shown in FIG. 4E, a second perpendicular loop segment 434 can be formed by again having needle 410 loop around the leaflet side edges and reenter the third aperture through the backside. This is repeated up to notch 234 to form a total of six parallel segments 436 and six perpendicular loop segments 434 in a forward direction, as shown in FIG. 4F. The stitch pattern can then be repeated in a reverse direction towards the bottom edges 222 of the leaflets through the previously formed apertures. Accordingly, each aperture can include two perpendicular loop segments 434 and parallel segments on the opposite sides can be formed from the parallel segments that were created in the forward direction, as shown in FIG. 4O. The method and stitches depicted in FIGS. 4A-4G can be applicable to leaflets 200, 300 discussed herein.

Stitch 446 and other stitches provided herein can improve the reliability of a seal formed along a stitch line, create fewer apertures through the leaflets, and simplify the stitching operation. Having fewer apertures can help minimize the occurrence of blood leakage through the apertures. The single continuous line of stitch 446 using a single row of apertures can minimize a width of a side edge portion needed to form a continuous seal along the side edges of the leaflets, thus providing a reduced restricted profile for prosthetic heart valves provided herein. For example, U.S. Pat.

No. 8,778,020 describes a variety of ways that leaflets can be sutured together using combinations of whip stitches and running stitches, but these stitches require additional apertures and multiple lines. Perpendicular loop segments 434 can stitch a plurality of leaflets together, similar to the whip stitches discussed in U.S. Pat. No. 8,778,020. Parallel segments 436 can secure valve leaflets to one another, similar to the running stitches discussed in U.S. Pat. No. 8,778,020. Although stitch 446 can provide an improved attachment between side edges of leaflets in prosthetic heart valves provided herein, some embodiments of prosthetic heart valves provided herein can use other stitch patterns, such as those described in U.S. Pat. No. 8,778,020, which is hereby incorporated by reference.

Important characteristics of the thread can include, but are not limited to, tensile strength, abrasion resistance and creep rupture resistance characteristics that allow the device to be delivered and implanted into a human anatomy. The thread used for suturing together portions of the heart valve, e.g., sides edges of the leaflets, can be composed of biocompatible materials that include, but are not limited to, polyethylenes such as ultra high molecular weight polyethylene (UHMWPE), polyesters (PET), and combinations thereof.

Referring back to FIGS. 1A and 1B, prosthetic heart valve 100 can include a tubular seal 130. Tubular seal 130 can be secured to bottom edges 222 (FIG. 2A) of the body portion 214 of at least one leaflet 200 by a circumferential running stitch 134 within prosthetic heart valve 100. Tubular seal 130 can be secured to expandable tubular member 110 by fasteners 136 and extended around the outside of expandable tubular member 110 to provide a seal that minimizes blood leakage around the leaflets 200 of an implanted prosthetic heart valve 100. The structure and materials of tubular seal 130 are discussed below in reference to FIGS. 6 and 7A-7E.

Figure 5A:
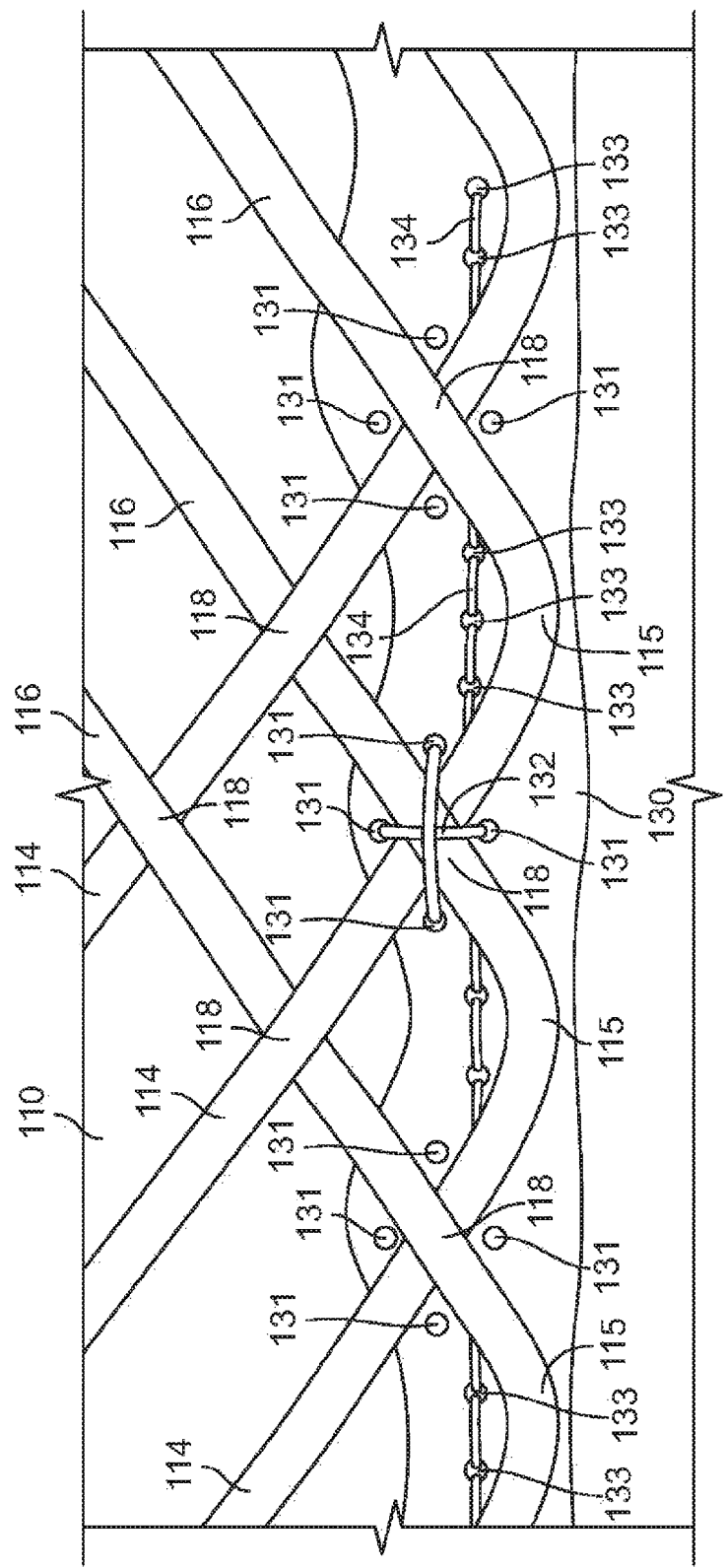
Figure 5C:
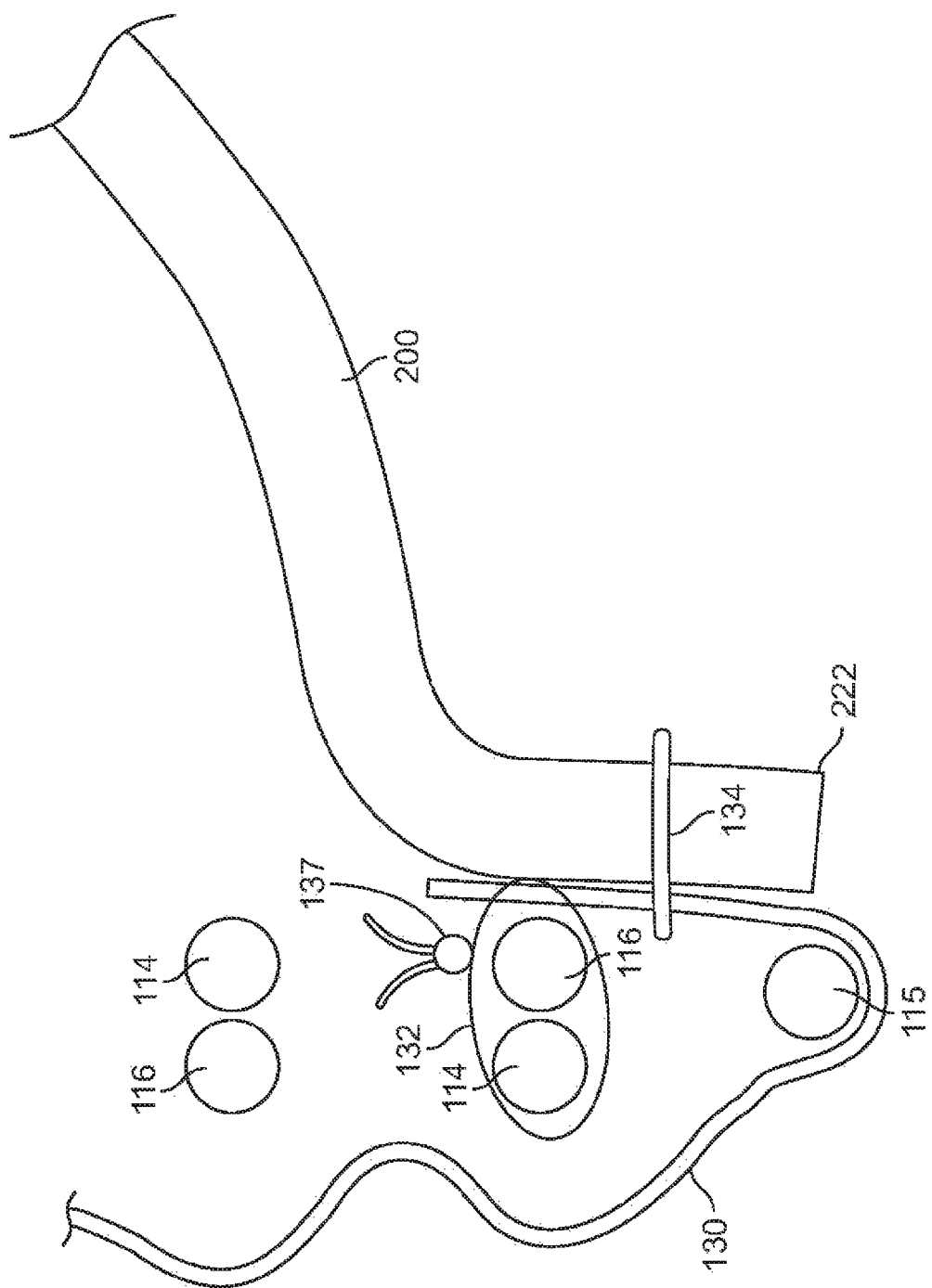

Referring to FIGS. 5A-5C, an improved tubular seal stitching pattern can include a cross stitch 132 between tubular seal 130 and expandable member 110. FIGS. 5A-5C illustrate how the tubular seal 130 can be secured to the expandable member 110, e.g., a braided stent, by a plurality of cross stitches connecting the tubular seal 130 to a pair of overlapping wire members of the braided stent. As shown in FIGS. 1A, 1B and 5A-5C, expandable member 110 can be a braided stent including one or more wires having a first set of segments 114 extending helically in a first direction and a second set of segments 116 extending helically in a second direction such that the first set of segments 114 cross the second set of segments 116 at intersection points 118. As shown, one or more wires can have inflow crowns 115 at an end of the braided stent where the wires transition from first segments 114 to second segments 116. In some cases, cross stitches 132 secure tubular seal 130 at an intersection 118 to two crossing segments 114, 116 of the braided stent. A separate circumferential running stitch 134 can be inserted into preformed apertures 133 to secure the adaptive seal to bottom edges 222 of leaflets 200 shown in FIGS. 2A and 2C. Cross-stitches around the intersections 118 can increase the strength of an attachment of tubular seal 130 to the expandable member 110 while also allowing for improved load transfer to the expandable member 110. In some cases, the cross stitches secure tubular seal 130 at intersections 118 located immediately above (proximal) the inflow crowns 115. Cross stitches 132 can be formed by passing two stitches 132a, 132b of a suture in orthogonal directions over the intersections 118 and through the tubular seal 130. In some cases, preformed apertures 131 for cross stitch 132 can be formed in the tubular seal 130. In some cases, a portion of the tubular seal 130 that is sutured by cross stitch 132 includes an internal fabric, such as those discussed below. Each cross stitch 132 can be knotted independently. As shown in FIG. 5C, cross stitches 132 each include a separate knot 137. Additionally, cross stitches 132 can be arranged to not pass through leaflets 200. Cross stitches 132 can be repeated at a plurality of intersections 118 (FIG. 5A) circumferentially around an inflow end of a prosthetic heart valve provided herein such that an entire circumference of tubular seal 130 is securely attached. In some cases, each intersection 118 immediately adjacent to inflow crowns 115 is sutured to tubular seal 130 via a cross stitch provided herein. The tubular seal stitching pattern provided herein can increase the strength of the attachment between the tubular seal 130 and the expandable member 110 while also allowing for improved load transfer to the expandable member 110 through the use of the plurality of cross stitches.

Tubular seal 130 can have any suitable structure. In some cases, tubular seal 130 can include an elastic material. In some cases, tubular seal 130 can include one or more layers of an elastomeric polymer. In some cases, tubular seal 130 can include a polycarbonate, polyurethane, silicone, polytetrafluoroethylene (PTFE), or a combination thereof. Other suitable materials include, but are not limited to, natural and synthetic rubbers, including cis-1,4-polyisoprene rubber, styrene/butadiene copolymers, polybutadiene rubber, styrene/isoprene/butadiene rubber, butyl rubber, halobutyl rubber polyurethane elastomers, including elastomers based on both aromatic and aliphatic isocyanates; flexible polyolefins, including flexible polyethylene and polypropylene homopolymers and copolymers; styrenic thermoplastic elastomers; polyamide elastomers; polyamide-ether elastomers; ester-ether or ester-ester elastomers; flexible ionomers; thermoplastic vulcanizates; flexible poly(vinyl chloride) homopolymers and copolymers; flexible acrylic polymers; and blends and alloys of these, such as poly(vinyl chloride) alloys like poly(vinyl chloride)-polyurethane alloys. In some cases, tubular seal 130 can include an aliphatic polycarbonate-based thermoplastic urethane. In some cases, tubular seal 130 can include an elastomeric polymer having a hardness ranging from 3.07 MPa to 9.9 MPa, or a durometer ranging from 75 Shore A to 75 Shore D using ASTM standard D2240 in force on Jan. 1, 2014. In some cases, tubular seal 130 can include a polymeric material having the mechanical properties shown in Table I below. Notably, all of the listed ASTM standards refers to the standard in force on Jan. 1, 2014.

TABLE I

| | | | | ASTM Standard |
|---|---|---|---|---|
| Durometer Range Available | 75 Shore A-75 Shore D | | | D2240 |
| Specific Gravity | 1.10-1.14 | | | D792 |
| Melt Flow | 2-26 g/10 min (205° C./3.26 kg) | | | D1238 |

| | MECHANICAL PROPERTY RANGES | | | ASTM Standard |
|---|---|---|---|---|
| Durometer | 75A-B20 | 55D | 75D | 75D |
| Ultimate Tensile Strength (psi) | 400-9000 | 5000-10000 | 3000-8000 | D638 |
| Tensile (psi) | | | | |
| @50% elongation | 350-650 | 1500-1800 | 3000-8000 | D638 |
| @100% elongation | 550-850 | 1800-2200 | 3000-8000 | D638 |
| @200% elongation | 600-1200 | 2800-4200 | | D638 |

TABLE I-continued

| @300% elongation | 1200-2000 | 4200-10000 | | D630 |
| Ultimate Elongation (%) | 350-750 | 200-400 | 100-300 | D638 |

In some cases, referring back to FIG. 1A, tubular seal 130 can include attachment structures to improve the attachment of the tubular seal 130 to leaflets 200 and/or expandable member 110.

Figure 7A:
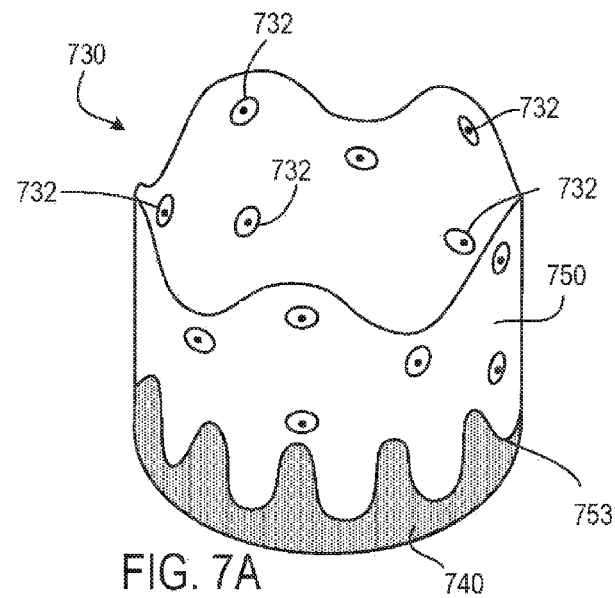
FIGS. 7A-7E depict exemplary tubular seals having a fabric positioned within a matrix that can be used in a prosthetic heart valve provided herein.
Figure 7B:
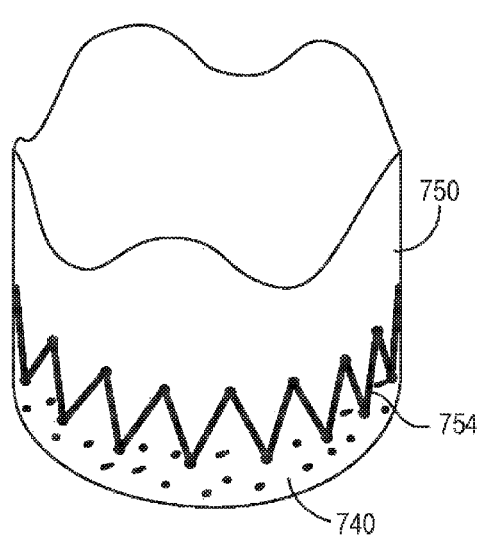

In some cases, as shown in FIG. 7A, a tubular seal 730 can include an inflow end section 740 and an outflow end section 750. The inflow end section 740 can include a fabric embedded within elastomeric material and the outflow end section 750 can include a plurality of grommets 732. The fabric of inflow end section 740 can be a woven material. In some cases, the fabric can have warp threads and/or weft threads. The fabric is composed of fibers having an average thread diameter from about 0.00002 inches to about 0.002 inches (or from about 0.5 microns to about 50 microns), more preferably from about 0.0008 inches to about 0.002 inches (or from about 20 micron to about 40 microns). In some cases, more preferably, the fabric is composed of fibers having a thread diameter of about 0.0011 inches (about 27 microns).

In some cases, the fabric can include non-elastomeric fibers. Suitable non-elastomeric fiber materials include, but are not limited to, polyolefins, polyesters such as PES 38/31 manufactured by SaatiTech, and polyamides. More particularly, the polyolefins may be, for example, one or more of polyethylene, polypropylene, polybutene, ethylene copolymers, propylene copolymers, and butene copolymers. Because the fabric can include non-elastic fibers, inflow end section 740 and outflow end section 750 can have different overall elastic properties. In some cases, tubular seal 730 can be used as a tubular seal 130 of prosthetic heart valve 100, as previously shown in FIG. 1A. In some cases, tubular seal 730 can be used in other prosthetic heart valves provided herein.

Figure 7C:
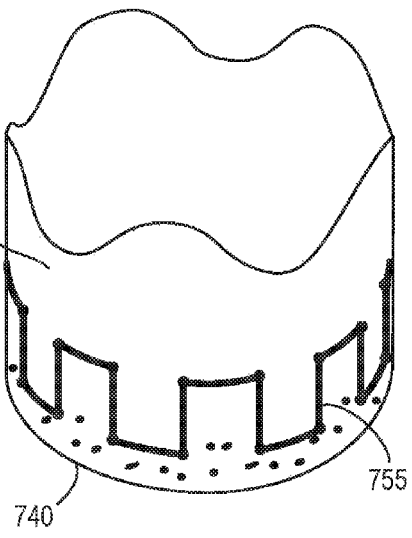
Figure 7D:
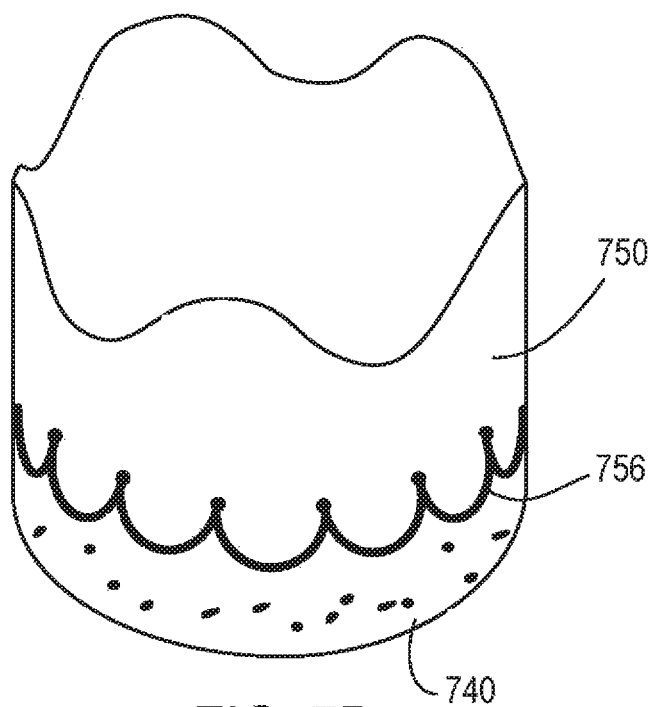

As shown in FIGS. 7A-7D, an interface 753 between the inflow end section 740 and the outflow end section 750 is non-linear due to a non-linear edge of fabric within the inflow end section 740. As shown in FIG. 7A, the non-linear edge can be sinusoidal 753. In some cases, as shown in FIGS. 7C-7D, the non-linear edge can be a zigzagged edge 754, a stepped edge 755, or a scalloped edge 756.

In some cases, inflow end section 740 can be thicker than outflow end section because of the presence of a fabric within inflow end section 740, 750. In some cases, inflow end section 740 can have a thickness of about 0.0028 inches (about 70 microns) and the outflow end section 750 can have a thickness of about 0.0020 inches (about 50 microns). Other suitable thicknesses for the inflow end section include thicknesses ranging from about 0.0020 inches to about 0.0035 inches (about 50 microns to about 90 microns), or more preferably, from about 0.0025 inches to about 0.0031 inches (about 60 microns to about 80 microns). Suitable thicknesses for the outflow end section include thicknesses ranging from about 0.0011 inches to about 0.0028 inches (about 30 microns to about 70 microns), or more preferably, from about 0.0016 inches to about 0.0023 inches (about 40 microns to about 60 microns). In some cases suitable thickness ratios of the inflow end section relative to the outflow end section can range from 1:1 to 1.2:1, from 1.2:1 to 1.4:1, from 1.4:1 to 1.5:1, and from 1.5:1 to 2:1. A non-linear edge can providing a non-linear interface between the inflow end section 740 and the outflow end section 750. A prosthetic heart valve with the non-linear interface may have an increased overall diameter that tapers more gradually when compared to a prosthetic heart valve that has a linear interface. The non-linear edge of the fabric can also gradually transition the change in elastic properties between the outflow end section 750 and the inflow end section 740, mitigating the formation of stress concentrators along the interface 753 that can cause tearing in the tubular member. Additionally, the shape of non-linear interface 753 can limit the propagation of tears.

In some cases, the fabric can be arranged in the inflow end section 740 to allow for the fabric within inflow end section 740 to stretch in axial and/or radial directions to allow the tubular seal to stretch along with an expandable member during implantation. When the fabric does not allow the tubular seal to adequately stretch, the seal can cause non-uniform crimping during manufacturing or damage the expandable member during device deployment. In some cases, a woven fabric can be arranged to have the warp and the waft extend in directions oblique to the axis of the tubular seal. This can allow the fabric to flex in radial and/or axial directions relative to the axis of the tubular seal, but limit the fabric from stretching in a direction oblique to the axis. In some cases, both the warp and the waft can extend at an angle between 30 degrees and 60 degrees with the axis of the tubular seal. In some cases, both the warp and the waft can extend at an angle between 5 degrees and 70 degrees with the axis of the tubular seal. In some cases, the warp and waft can be arranged within the tubular member 730 to form an angle of about degrees with the axis of the tubular seal. In some cases, the fabric can be a knit fabric arranged to allow for a predetermined amount of stretch in the axial and/or radial directions. Limiting the fabric within inflow end section 740 from stretching in a direction oblique to the axis can prevent the fabric from bunching and minimize non-uniform crimping during manufacturing.

Additional exemplary tubular seals including a fabric and grommets are described in U.S. Patent Application No. 2013/0090729, which is hereby incorporated by reference in its entirety. For example, U.S. Pat. No. 8,778,020 describes a seal that includes a multilayer, cylindrical seal body having projections alternating with recesses along the proximal edge of the seal body with proximal reinforcing grommets and a distal reinforcing band, which may be formed from a woven or nonwoven fabric and either incorporated within the interior of the multilayer seal body or adhered to the surface thereof.

In some cases, tubular seals described in U.S. Patent Application No. 2013/0090729 can be modified to include a fabric arrangement that allows a seal to stretch in axial and/or radial directions. In some cases, elastomeric materials provided herein can be incorporated into the tubular seals disclosed in U.S. Patent Application No. 2013/0090729. In some cases, the tubular seals described in U.S. Patent Application No. 2013/0090729 can be modified to include the non-linear interface 753 provided herein.

Referring back to FIG. 7A, tubular seal 730 can be created by producing one or more layers of elastomeric polymer, applying the fabric and grommets 732 to the one or more layers of elastomeric polymer, and overcoating the fabric and grommets 732 with one or more additional layers of elastomeric material. In some cases, different layers can have different elastomeric properties. In some cases, tubular seals (e.g., 130, 730, or 760) can include a radially innermost layer including at least one elastomeric polymer, e.g., a polycarbonate and a polyurethane; a radially outermost layer including at least one elastomeric polymer, e.g., a polycarbonate and a polyurethane; and at least one inner layer disposed between the radially outermost layer and a radially innermost layer. In some cases, the modulus of elasticity of the innermost layer is less than the modulus of elasticity of the radially innermost outer layer and the modulus of elasticity of the radially outermost outer layer. In some cases, the elongation to break of the inner layer is greater than the elongation to break of the radially innermost outer layer and the elongation to break of the radially outermost outer layer. Although the radially innermost outer layer and the radially outermost outer layer have been depicted as including the same material, it will be appreciated that they may be compositionally the same or different.

Figure 6:
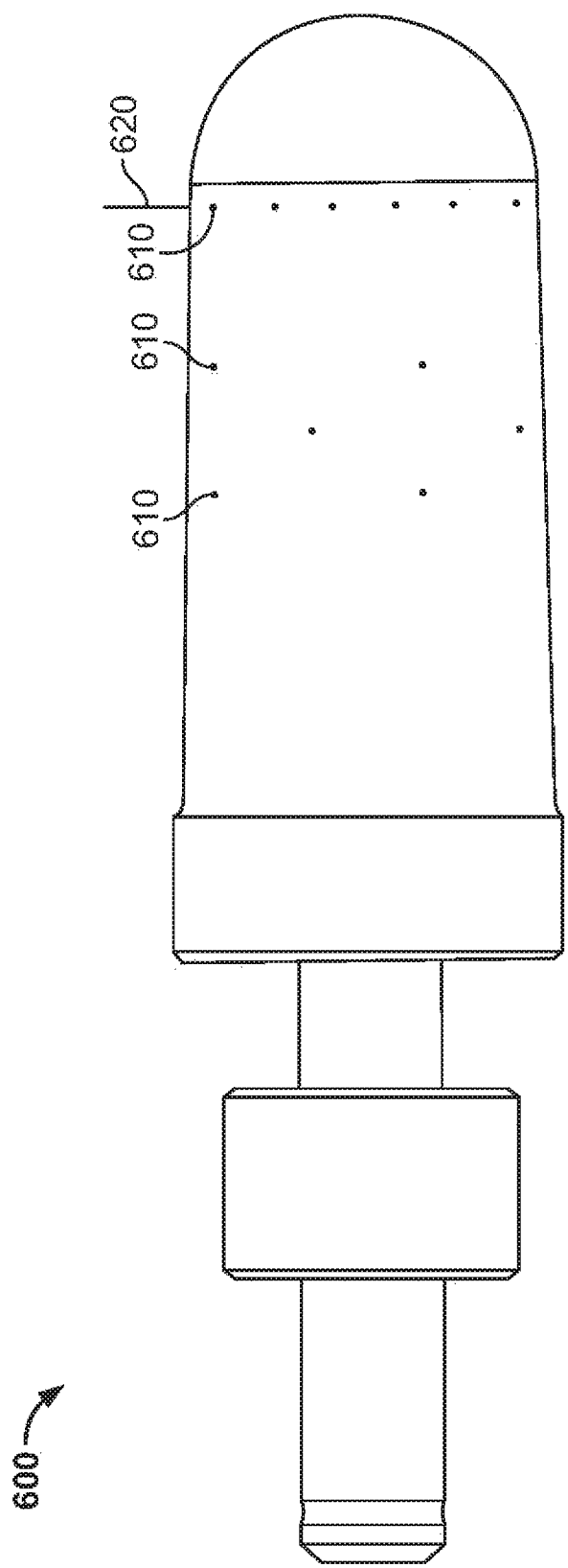
FIG. 6 depicts an apparatus that can be used to form a tubular seal provided herein.

The multilayer tubular seals provided herein (e.g., 130, 730, 760) may be formed in a variety of ways. In some cases, multilayer tubular seals provided herein may be formed by successive applications of a polymer solution to an appropriately shaped mandrel, such as that illustrated in FIG. 6. Following a careful cleaning of the mandrel 600, the mandrel may be mounted to an appropriate holding fixture in a spray booth. A first coating composition including a carrier and at least one polymer may be applied to the mandrel 600 and subsequently dried to form a first coated mandrel. In some cases, the first coating composition includes one or more elastomeric polymers, e.g., polycarbonate and/or a polyurethane, and a volatile carrier. The coating composition may be applied as a single layer or multiple layers to achieve the desired dried coating thickness. The grommets 732 (FIG. 7A) and the fabric may be positioned on the first coated mandrel by inserting locating pins 620 in apertures 610 in the tapered mandrel 600 which align with corresponding perforations 30 provided in the grommets 32, 34, 36 and the fabric 40. In FIG. 6, only one pin 620 has been illustrated for clarity. In some instances, it may be desirable to secure the plurality of grommets 732 and the fabric to the mandrel or to an underlying coating layer by applying a drop of a first coating composition, or other adhesive composition, to each item to ensure that it remains properly positioned during subsequent processing. The fabric can be cut to a suitable shape having a non-linear edge using any suitable method. In some cases, the fabric can be die cut. In some cases, the fabric can be cut with a blade. In some cases, the fabric can be cut using a femtosecond laser. In some cases, a femtosecond laser cut fabric mitigate the chances of forming stress concentrators along the edge of the fabric.

A second coating composition including a carrier and at least one polymer may be applied to the first coated mandrel, the fabric, and the plurality of grommets. In some cases, the second coating composition includes one or more elastomeric polymers, e.g. polycarbonate and/or a polyurethane, and a volatile carrier. The carrier of the second coating composition may be removed, thereby forming a second coated mandrel. The second coating composition may be applied as a single layer or as multiple layers to achieve the desired dried coating thickness. In some cases, the second coating composition may be different from the first coating composition. In some cases, the second coating composition may be composed of the same material as the first coating composition.

In some cases, a third coating composition including a carrier and at least one polymer may be applied to the second coated mandrel. In some cases, the third coating composition includes one or more elastomeric polymers, e.g. polycarbonate and/or a polyurethane, and a volatile carrier. The carrier of the third coating composition may be removed thereby forming a tubular seal precursor. The third coating composition may be applied as a single layer or as multiple layers to achieve the desired dried coating thickness. In some cases, the third coating composition may be different from the first coating composition. In some cases, the third coating composition may be the same as the first coating composition. In some cases, the third coating composition may be different from the second coating composition. In some cases, the third coating composition may be the same as the second coating composition. Following removal of the carrier from the third coating composition, the tubular seal precursor may be inspected to ensure that it is fully formed and meets dimensional specifications, such as a thickness specification. In some cases, a suitable thickness for the tubular seal precursor can range from about 0.001 inches to about 0.0030 inches (about 30 microns to about 75 microns) or from about 0.002 inches to about 0.0047 inches (about 50 microns to about 120 microns). Other suitable thicknesses for the tubular seal precursor include a range from about 0.0008 inches to about 0.002 inches (about 20 microns to about 40 microns), about 0.001 inches to about 0.002 inches (about 30 microns to about 50 microns), about 0.002 inches to about 0.0029 inches (about 50 microns to about 75 microns), about 0.002 inches to about 0.004 inches (about 50 microns to about 100 microns), about 0.004 inches to about 0.0047 inches (about 100 microns to about 120 microns), about 0.004 inches to about 0.0059 inches (about 100 microns to about 150 microns), about 0.0059 inches to about 0.0079 inches (about 150 microns to about 200 microns), as well as any thickness value within any of the listed ranges.

In some cases, the tubular seal precursor may be inspected to ensure that it meets certain functional specifications, e.g., tensile and frictional specifications. The tubular seal precursor may then be trimmed by laser cutting, or blade cutting, to conform to dimensional specifications and removed from the tapered seal-forming mandrel as a formed tubular seal. In some cases, at least some preformed apertures for suturing tubular seal to expandable member 110 and/or leaflets 200 can be performed by laser cutting. In some cases, at least some of the grommets may be formed by a laser cutting operation performed on a tubular seal precursor. In some cases, grommets 732 of FIG. 7A may be added to the multilayer, generally cylindrical seal, in a step not illustrated, as a proximal band. Subsequent laser cutting of the tubular seal precursor would then simultaneously form grommets 732 by removing the portions of the proximal band located between the projections.

In some cases, coating compositions may be selected to provide a relatively stiff dried polymer such as a dried polymer having a Shore D hardness of about 55, or a hardness of about 6.21 Megapascals (Mpa). In some cases, coating compositions may be selected to provide a relatively elastomeric dried polymer such as a dried polymer having a Shore A hardness of about 80, or a hardness of about 3.45 MPa. In some cases, the first and third dried polymer layers may have a Shore D hardness of 55, or a hardness of 6.21 MPa, and the second layer may have a Shore A hardness of 80, or a hardness of 3.45 MPa.

Although in some cases described above, three polymer layers were employed, it will be appreciated that a greater or lesser number of layers may be employed and that each of the three or more layers may include two or more sublayers. In some cases, the plurality of grommets and the fabric can be positioned between the first and second coating layers. In some cases, the plurality of grommets and the fabric can be positioned elsewhere within the tubular seal, e.g., within a layer, or on the radially innermost or radially outermost surface of the tubular seal.

The mandrel 600 of FIG. 6 includes a taper which results in a tubular seal having a slightly smaller diameter proximal end compared to the diameter of the distal end. In some cases, the diameter of the proximal end can include a diameter reduction of about 3% to about 30% as compared to the diameter of the distal end. The taper allows the tubular seal to be removed from the mandrel with relative ease upon completion of the fabrication process. The smaller proximal diameter of the tubular seal tends to cause the proximal projections to lie more firmly against an anchor element of the replacement heart valve. In some cases, the surface of the mandrel may be textured to create a tubular seal with a reduced contact area. In some cases the mandrel can be textured using a bead blasting process. In combination with the selection of a relatively hard outer layer, a textured seal surface is believed to result in a lower friction surface.

Figure 7E:
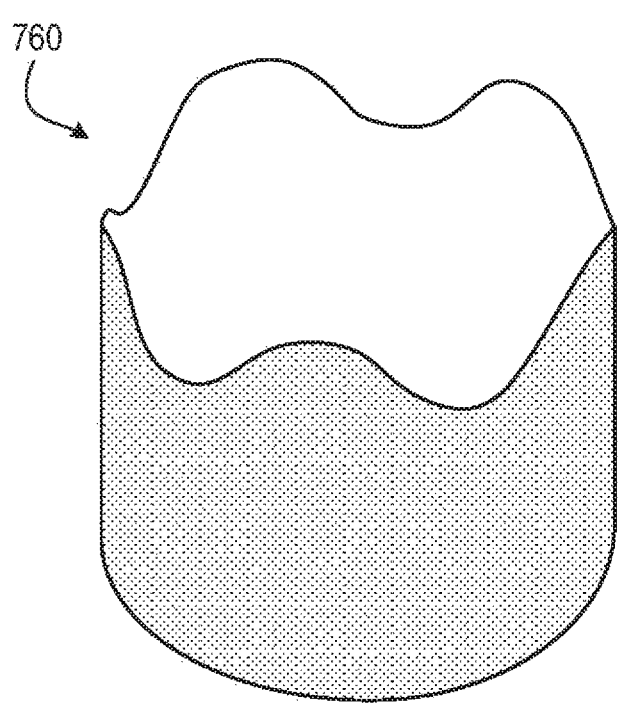

As shown in FIG. 7E, a tubular seal 760 can include a woven or non-woven fabric embedded throughout a polymer or metal matrix structure. In some cases, at least one leaflet of the heart valve can be secured to the tubular seal in a portion of the tubular seal including the woven or non-woven fabric to minimize blood leakage between the tubular seal and the leaflets.

In some cases, the matrix structure can be made of elastomeric material. In some cases, tubular seal 760 can be made of the fabric alone. The fabric can include non-elastic fibers arranged to allow for the tubular seal 760 to stretch in axial and/or radial directions relative to the axis of the tubular seal 760. In some cases, the non-elastic fibers can be arranged within the tubular member 760 to form an angle of about 45 degrees with the axis of the tubular seal. In some cases, the fabric can be a knit fabric arranged to allow for a predetermined amount of stretch in the axial and/or radial directions. In some cases, the fabric can be made of polymeric materials that include, but are not limited to, polyesters, polyolefins such as polyethylene and polypropylene, polyamides, nylons, and combinations thereof. In some cases, the fabric can have a thickness ranging from about 0.002 inches to about 0.003 inches (about 40 to about 80 microns). In some cases, the fabric can be woven such that spacings between individual fibers create openings in the fabric that together constitutes from about 20% to about 40% of a fabric surface.

A number of embodiments of the invention have been described. Nevertheless, it will be understood that various modifications may be made without departing from the spirit and scope of the invention. Accordingly, other embodiments are within the scope of the following claims.

What is claimed:

1. A prosthetic heart valve comprising at least one leaflet having a body portion and two opposite sleeve portions, the body portion being defined by at least two side edges adjacent each sleeve portion, the at least one leaflet defining at least one notch between at least one of the two side edges and the adjacent sleeve portion;
    wherein the at least one leaflet is secured to at least a second leaflet along at least one side edge;
    wherein the at least one leaflet is secured to the at least second leaflet by a running stitch;
    wherein the running stitch is a square stitch.

2. The prosthetic heart valve of claim 1, wherein the prosthetic heart valve comprises three leaflets each defining at least one notch between at least one side edge and an adjacent sleeve portion.

3. The prosthetic heart valve of claim 1, wherein the at least one leaflet defines a notch between each of the two side edges and each adjacent sleeve portion.

4. The prosthetic heart valve of claim 1, further comprising an expandable member and at least two anchor elements securing each of the sleeve portions to the expandable member.

5. The prosthetic heart valve of claim 4, wherein the prosthetic heart valve comprises 3 leaflets and three anchor elements, each leaflet being secured to each of the other leaflets along the side edges of each leaflet.

6. A prosthetic heart valve comprising at least one leaflet having a body portion and two opposite sleeve portions, the body portion being defined by at least two side edges adjacent each sleeve portion, the at least one leaflet defining at least one notch between at least one of the two side edges and the adjacent sleeve portion;
    further comprising an expandable member and at least two anchor elements securing each of the sleeve portions to the expandable member;
    wherein the prosthetic heart valve comprises 3 leaflets and three anchor elements, each leaflet being secured to each of the other leaflets along the side edges of each leaflet;
    further comprising a plurality of support elements each supporting sleeve portions each leaflet along a line approximately aligned with secured portions of the side edges of each leaflet.

7. A prosthetic heart valve comprising at least one leaflet having a body portion and two opposite sleeve portions, the body portion being defined by at least two side edges adjacent each sleeve portion, the at least one leaflet defining at least one notch between at least one of the two side edges and the adjacent sleeve portion;
    further comprising an expandable member and at least two anchor elements securing each of the sleeve portions to the expandable member;
    wherein the prosthetic heart valve comprises 3 leaflets and three anchor elements, each leaflet being secured to each of the other leaflets along the side edges of each leaflet;
    further comprising a plurality of support elements each supporting sleeve portions each leaflet along a line approximately aligned with secured portions of the side edges of each leaflet;
    wherein each leaflet is defined by at least two notches, wherein each notch is aligned with the secured portions of the side edges of each leaflet and a supported portion of the sleeve portions.

8. The prosthetic heart valve of claim 1, wherein the at least one leaflet comprises bovine or porcine pericardium tissue.

9. The prosthetic heart valve of claim 1, wherein the at least one leaflet comprises a synthetic material.

10. The prosthetic heart valve of claim 6, wherein the at least one leaflet comprises bovine or porcine pericardium tissue.

11. The prosthetic heart valve of claim 6, wherein the at least one leaflet comprises a synthetic material.

12. The prosthetic heart valve of claim 7, wherein the at least one leaflet comprises bovine or porcine pericardium tissue.

13. The prosthetic heart valve of claim 7, wherein the at least one leaflet comprises a synthetic material.

14. The prosthetic heart valve of claim 1, further comprising:
    an expandable tubular member, wherein each sleeve portion is secured to the tubular member; and a tubular seal secured to a bottom edge of each leaflet and along an outer portion of the expandable tubular member.

15. The prosthetic heart valve of claim 6, further comprising a tubular seal secured to a bottom edge of each leaflet and along an outer portion of the expandable tubular member.

16. The prosthetic heart valve of claim 7, further comprising a tubular seal secured to a bottom edge of each leaflet and along an outer portion of the expandable tubular member.

* * * * *